US009421388B2

(12) United States Patent
John

(10) Patent No.: US 9,421,388 B2
(45) Date of Patent: Aug. 23, 2016

(54) POWER GENERATION FOR IMPLANTABLE DEVICES

(71) Applicant: WiTricity Corporation, Watertown, MA (US)

(72) Inventor: Michael Sasha John, Larchmont, NY (US)

(73) Assignee: WiTricity Corporation, Watertown, MA (US)

( * ) Notice: Subject to any disclaimer, the term of this patent is extended or adjusted under 35 U.S.C. 154(b) by 0 days.

(21) Appl. No.: 14/454,349

(22) Filed: Aug. 7, 2014

(65) Prior Publication Data

US 2015/0080981 A1    Mar. 19, 2015

Related U.S. Application Data

(63) Continuation-in-part of application No. 12/131,910, filed on Jun. 2, 2008, now Pat. No. 8,805,530.

(60) Provisional application No. 60/977,086, filed on Oct. 2, 2007, provisional application No. 60/941,286, filed on Jun. 1, 2007, provisional application No. 60/941,287, filed on Jun. 1, 2007.

(51) Int. Cl.
*A61N 1/00* (2006.01)
*A61N 1/378* (2006.01)
*A61N 1/372* (2006.01)

(52) U.S. Cl.
CPC ............ *A61N 1/3787* (2013.01); *A61N 1/3785* (2013.01); *A61N 1/37252* (2013.01)

(58) Field of Classification Search
CPC ... A61N 1/378; A61N 1/3782; A61N 1/3785; A61N 1/3787
See application file for complete search history.

(56) References Cited

U.S. PATENT DOCUMENTS

| 645,576 A | 3/1900 | Tesla |
|---|---|---|
| 649,621 A | 5/1900 | Tesla |

(Continued)

FOREIGN PATENT DOCUMENTS

| CA | 142352 | 8/1912 |
|---|---|---|
| CN | 102239633 | 11/2011 |

(Continued)

OTHER PUBLICATIONS

"Intel CTO Says Gap between Humans, Machines Will Close by 2050", *Intel News Release*, (See intel.com/.../20080821comp. htm?iid=S . . . ) (Printed Nov. 6, 2009).

(Continued)

*Primary Examiner* — Scott Getzow
(74) *Attorney, Agent, or Firm* — Fish & Richardson P.C.

(57) ABSTRACT

A rechargeable medical system comprised of an implanted device, rechargeable power storage operatively connected to the implantable device, a charging module operatively connected to the rechargeable storage, and external devices including a patient programmer and external charging means. The charging module can harvest at least one of thermal, photovoltaic, movement, RF, and magnetic energy to generate electrical power. The system has components for charging the storage from the generated power, and for measuring power generation, usage and reserve levels. The system provides for physically initiating and disrupting charging operations, for generating and communicating signals relevant to power harvesting, for monitoring, providing, and displaying data related to energy generation and energy generation criteria, and for tracking historical harvesting and energy consumption. The system may also have long-range and short-range wireless power harvesting capability.

23 Claims, 6 Drawing Sheets

(56) References Cited

U.S. PATENT DOCUMENTS

| | | |
|---|---|---|
| 787,412 A | 4/1905 | Tesla |
| 1,119,732 A | 12/1914 | Tesla |
| 2,133,494 A | 10/1938 | Waters |
| 3,517,350 A | 6/1970 | Beaver |
| 3,535,543 A | 10/1970 | Dailey |
| 3,780,425 A | 12/1973 | Penn et al. |
| 3,871,176 A | 3/1975 | Schukei |
| 4,088,999 A | 5/1978 | Fletcher et al. |
| 4,095,998 A | 6/1978 | Hanson |
| 4,180,795 A | 12/1979 | Matsuda et al. |
| 4,280,129 A | 7/1981 | Wells |
| 4,450,431 A | 5/1984 | Hochstein |
| 4,588,978 A | 5/1986 | Allen |
| 5,027,709 A | 7/1991 | Slagle |
| 5,033,295 A | 7/1991 | Schmid et al. |
| 5,034,658 A | 7/1991 | Hiering et al. |
| 5,053,774 A | 10/1991 | Schuermann et al. |
| 5,070,293 A | 12/1991 | Ishii et al. |
| 5,118,997 A | 6/1992 | El-Hamamsy |
| 5,216,402 A | 6/1993 | Carosa |
| 5,229,652 A | 7/1993 | Hough |
| 5,287,112 A | 2/1994 | Schuermann |
| 5,341,083 A | 8/1994 | Klontz et al. |
| 5,367,242 A | 11/1994 | Hulman |
| 5,374,930 A | 12/1994 | Schuermann |
| 5,408,209 A | 4/1995 | Tanzer et al. |
| 5,437,057 A | 7/1995 | Richley et al. |
| 5,455,467 A | 10/1995 | Young et al. |
| 5,493,691 A | 2/1996 | Barrett |
| 5,522,856 A | 6/1996 | Reineman |
| 5,528,113 A | 6/1996 | Boys et al. |
| 5,541,604 A | 7/1996 | Meier |
| 5,550,452 A | 8/1996 | Shirai et al. |
| 5,565,763 A | 10/1996 | Arrendale et al. |
| 5,630,835 A | 5/1997 | Brownlee |
| 5,697,956 A | 12/1997 | Bornzin |
| 5,703,461 A | 12/1997 | Minoshima et al. |
| 5,703,573 A | 12/1997 | Fujimoto et al. |
| 5,710,413 A | 1/1998 | King et al. |
| 5,742,471 A | 4/1998 | Barbee, Jr. et al. |
| 5,821,728 A | 10/1998 | Sshwind |
| 5,821,731 A | 10/1998 | Kuki et al. |
| 5,864,323 A | 1/1999 | Berthon |
| 5,898,579 A | 4/1999 | Boys et al. |
| 5,903,134 A | 5/1999 | Takeuchi |
| 5,923,544 A | 7/1999 | Urano |
| 5,940,509 A | 8/1999 | Jovanovich et al. |
| 5,957,956 A | 9/1999 | Kroll et al. |
| 5,959,245 A | 9/1999 | Moe et al. |
| 5,986,895 A | 11/1999 | Stewart et al. |
| 5,993,996 A | 11/1999 | Firsich |
| 5,999,308 A | 12/1999 | Nelson et al. |
| 6,012,659 A | 1/2000 | Nakazawa et al. |
| 6,047,214 A | 4/2000 | Mueller et al. |
| 6,066,163 A | 5/2000 | John |
| 6,067,473 A | 5/2000 | Greeninger et al. |
| 6,108,579 A * | 8/2000 | Snell et al. ............... 607/29 |
| 6,127,799 A * | 10/2000 | Krishnan ............... 320/104 |
| 6,176,433 B1 | 1/2001 | Uesaka et al. |
| 6,184,651 B1 | 2/2001 | Fernandez et al. |
| 6,207,887 B1 | 3/2001 | Bass et al. |
| 6,232,841 B1 | 5/2001 | Bartlett et al. |
| 6,238,387 B1 | 5/2001 | Miller, III |
| 6,252,762 B1 | 6/2001 | Amatucci |
| 6,436,299 B1 | 8/2002 | Baarman et al. |
| 6,450,946 B1 | 9/2002 | Forsell |
| 6,452,465 B1 | 9/2002 | Brown et al. |
| 6,459,218 B2 | 10/2002 | Boys et al. |
| 6,473,028 B1 | 10/2002 | Luc |
| 6,483,202 B1 | 11/2002 | Boys |
| 6,515,878 B1 | 2/2003 | Meins et al. |
| 6,535,133 B2 | 3/2003 | Gohara |
| 6,561,975 B1 | 5/2003 | Pool et al. |
| 6,563,425 B2 | 5/2003 | Nicholson et al. |
| 6,597,076 B2 | 7/2003 | Scheible et al. |
| 6,609,023 B1 | 8/2003 | Fischell et al. |
| 6,631,072 B1 | 10/2003 | Paul et al. |
| 6,650,227 B1 | 11/2003 | Bradin |
| 6,664,770 B1 | 12/2003 | Bartels |
| 6,673,250 B2 | 1/2004 | Kuennen et al. |
| 6,683,256 B2 | 1/2004 | Kao |
| 6,696,647 B2 | 2/2004 | Ono et al. |
| 6,703,921 B1 | 3/2004 | Wuidart et al. |
| 6,731,071 B2 | 5/2004 | Baarman |
| 6,749,119 B2 | 6/2004 | Scheible et al. |
| 6,772,011 B2 | 8/2004 | Dolgin |
| 6,798,716 B1 | 9/2004 | Charych |
| 6,803,744 B1 | 10/2004 | Sabo |
| 6,806,649 B2 | 10/2004 | Mollema et al. |
| 6,812,645 B2 | 11/2004 | Baarman |
| 6,825,620 B2 | 11/2004 | Kuennen et al. |
| 6,831,417 B2 | 12/2004 | Baarman |
| 6,839,035 B1 | 1/2005 | Addonisio et al. |
| 6,844,702 B2 | 1/2005 | Giannopoulos et al. |
| 6,856,291 B2 | 2/2005 | Mickle et al. |
| 6,858,970 B2 | 2/2005 | Malkin et al. |
| 6,906,495 B2 | 6/2005 | Cheng et al. |
| 6,917,163 B2 | 7/2005 | Baarman |
| 6,917,431 B2 | 7/2005 | Soljacic et al. |
| 6,937,130 B2 | 8/2005 | Scheible et al. |
| 6,960,968 B2 | 11/2005 | Odendaal et al. |
| 6,961,619 B2 | 11/2005 | Casey |
| 6,967,462 B1 | 11/2005 | Landis |
| 6,975,198 B2 | 12/2005 | Baarman |
| 6,988,026 B2 | 1/2006 | Breed et al. |
| 7,027,311 B2 | 4/2006 | Vanderelli et al. |
| 7,035,076 B1 | 4/2006 | Stevenson |
| 7,042,196 B2 | 5/2006 | Ka-Lai et al. |
| 7,069,064 B2 | 6/2006 | Govorgian et al. |
| 7,084,605 B2 | 8/2006 | Mickle et al. |
| 7,116,200 B2 | 10/2006 | Baarman et al. |
| 7,118,240 B2 | 10/2006 | Baarman et al. |
| 7,126,450 B2 | 10/2006 | Baarman et al. |
| 7,127,293 B2 | 10/2006 | MacDonald |
| 7,132,918 B2 | 11/2006 | Baarman et al. |
| 7,147,604 B1 | 12/2006 | Allen et al. |
| 7,180,248 B2 | 2/2007 | Kuennen et al. |
| 7,191,007 B2 | 3/2007 | Desai et al. |
| 7,193,418 B2 | 3/2007 | Freytag |
| D541,322 S | 4/2007 | Garrett et al. |
| 7,212,414 B2 | 5/2007 | Baarman |
| 7,233,137 B2 | 6/2007 | Nakamura et al. |
| D545,855 S | 7/2007 | Garrett et al. |
| 7,239,110 B2 | 7/2007 | Cheng et al. |
| 7,248,017 B2 | 7/2007 | Cheng et al. |
| 7,251,527 B2 | 7/2007 | Lyden |
| 7,288,918 B2 | 10/2007 | DiStefano |
| 7,340,304 B2 | 3/2008 | MacDonald |
| 7,375,492 B2 | 5/2008 | Calhoon et al. |
| 7,375,493 B2 | 5/2008 | Calhoon et al. |
| 7,378,817 B2 | 5/2008 | Calhoon et al. |
| 7,382,636 B2 | 6/2008 | Baarman et al. |
| 7,385,357 B2 | 6/2008 | Kuennen et al. |
| 7,443,135 B2 | 10/2008 | Cho |
| 7,462,951 B1 | 12/2008 | Baarman |
| 7,466,213 B2 | 12/2008 | Lobl et al. |
| 7,471,062 B2 | 12/2008 | Bruning |
| 7,474,058 B2 | 1/2009 | Baarman |
| 7,492,247 B2 | 2/2009 | Schmidt et al. |
| 7,514,818 B2 | 4/2009 | Abe et al. |
| 7,518,267 B2 | 4/2009 | Baarman |
| 7,521,890 B2 | 4/2009 | Lee et al. |
| 7,525,283 B2 | 4/2009 | Cheng et al. |
| 7,545,337 B2 | 6/2009 | Guenther |
| 7,554,316 B2 | 6/2009 | Stevens et al. |
| 7,599,743 B2 | 10/2009 | Hassler, Jr. et al. |
| 7,615,936 B2 | 11/2009 | Baarman et al. |
| 7,639,514 B2 | 12/2009 | Baarman |
| 7,741,734 B2 | 6/2010 | Joannopoulos et al. |
| 7,795,708 B2 | 9/2010 | Katti |
| 7,825,543 B2 | 11/2010 | Karalis et al. |
| 7,825,544 B2 | 11/2010 | Jansen et al. |
| 7,835,417 B2 | 11/2010 | Heideman et al. |
| 7,843,288 B2 | 11/2010 | Lee et al. |

(56) References Cited

U.S. PATENT DOCUMENTS

| | | |
|---|---|---|
| 7,844,306 B2 | 11/2010 | Shearer et al. |
| 7,863,859 B2 | 1/2011 | Soar |
| 7,880,337 B2 | 2/2011 | Farkas |
| 7,884,697 B2 | 2/2011 | Wei et al. |
| 7,885,050 B2 | 2/2011 | Lee |
| 7,919,886 B2 | 4/2011 | Tanaka |
| 7,923,870 B2 | 4/2011 | Jin |
| 7,932,798 B2 | 4/2011 | Tolle et al. |
| 7,948,209 B2 | 5/2011 | Jung |
| 7,952,322 B2 | 5/2011 | Partovi et al. |
| 7,963,941 B2 | 6/2011 | Wilk |
| 7,969,045 B2 | 6/2011 | Schmidt et al. |
| 7,994,880 B2 | 8/2011 | Chen et al. |
| 7,999,506 B1 | 8/2011 | Hollar et al. |
| 8,022,576 B2 | 9/2011 | Joannopoulos et al. |
| 8,035,255 B2 | 10/2011 | Kurs et al. |
| 8,076,800 B2 | 12/2011 | Joannopoulos et al. |
| 8,076,801 B2 | 12/2011 | Karalis et al. |
| 8,084,889 B2 | 12/2011 | Joannopoulos et al. |
| 8,097,983 B2 | 1/2012 | Karalis et al. |
| 8,106,539 B2 | 1/2012 | Schatz et al. |
| 8,115,448 B2 | 2/2012 | John |
| 8,131,378 B2 | 3/2012 | Greenberg et al. |
| 8,178,995 B2 | 5/2012 | Amano et al. |
| 8,193,769 B2 | 6/2012 | Azancot et al. |
| 8,212,414 B2 | 7/2012 | Howard et al. |
| 8,260,200 B2 | 9/2012 | Shimizu et al. |
| 8,304,935 B2 | 11/2012 | Karalis et al. |
| 8,324,759 B2 | 12/2012 | Karalis et al. |
| 8,334,620 B2 | 12/2012 | Park et al. |
| 8,362,651 B2 | 1/2013 | Hamam et al. |
| 8,395,282 B2 | 3/2013 | Joannopoulos et al. |
| 8,395,283 B2 | 3/2013 | Joannopoulos et al. |
| 8,400,017 B2 | 3/2013 | Kurs et al. |
| 8,400,018 B2 | 3/2013 | Joannopoulos et al. |
| 8,400,019 B2 | 3/2013 | Joannopoulos et al. |
| 8,400,020 B2 | 3/2013 | Joannopoulos et al. |
| 8,400,021 B2 | 3/2013 | Joannopoulos et al. |
| 8,400,022 B2 | 3/2013 | Joannopoulos et al. |
| 8,400,023 B2 | 3/2013 | Joannopoulos et al. |
| 8,400,024 B2 | 3/2013 | Joannopoulos et al. |
| 8,410,636 B2 | 4/2013 | Kurs et al. |
| 8,441,154 B2 | 5/2013 | Karalis et al. |
| 8,457,547 B2 | 6/2013 | Meskens |
| 8,461,719 B2 | 6/2013 | Kesler et al. |
| 8,461,720 B2 | 6/2013 | Kurs et al. |
| 8,461,721 B2 | 6/2013 | Karalis et al. |
| 8,461,722 B2 | 6/2013 | Kurs et al. |
| 8,461,817 B2 | 6/2013 | Martin et al. |
| 8,466,583 B2 | 6/2013 | Karalis et al. |
| 8,471,410 B2 | 6/2013 | Karalis et al. |
| 8,476,788 B2 | 7/2013 | Karalis et al. |
| 8,482,157 B2 | 7/2013 | Cook et al. |
| 8,482,158 B2 | 7/2013 | Kurs et al. |
| 8,487,480 B1 | 7/2013 | Kesler et al. |
| 8,497,601 B2 | 7/2013 | Hall et al. |
| 8,552,592 B2 | 10/2013 | Schatz et al. |
| 8,569,914 B2 | 10/2013 | Karalis et al. |
| 8,587,153 B2 | 11/2013 | Schatz et al. |
| 8,587,155 B2 | 11/2013 | Giler et al. |
| 8,598,743 B2 | 12/2013 | Hall et al. |
| 8,618,696 B2 | 12/2013 | Karalis et al. |
| 8,629,578 B2 | 1/2014 | Kurs et al. |
| 8,643,326 B2 | 2/2014 | Campanella et al. |
| 2002/0032471 A1 | 3/2002 | Loftin et al. |
| 2002/0105343 A1 | 8/2002 | Scheible et al. |
| 2002/0118004 A1 | 8/2002 | Scheible et al. |
| 2002/0130642 A1 | 9/2002 | Ettes et al. |
| 2002/0167294 A1 | 11/2002 | Odaohhara |
| 2003/0038641 A1 | 2/2003 | Scheible |
| 2003/0062794 A1 | 4/2003 | Scheible et al. |
| 2003/0062980 A1 | 4/2003 | Scheible et al. |
| 2003/0071034 A1 | 4/2003 | Thompson et al. |
| 2003/0124050 A1 | 7/2003 | Yadav et al. |
| 2003/0126948 A1 | 7/2003 | Yadav et al. |
| 2003/0160590 A1 | 8/2003 | Schaefer et al. |
| 2003/0199778 A1 | 10/2003 | Mickle et al. |
| 2003/0214255 A1 | 11/2003 | Baarman et al. |
| 2004/0000974 A1 | 1/2004 | Odenaal et al. |
| 2004/0026998 A1 | 2/2004 | Henriott et al. |
| 2004/0100338 A1 | 5/2004 | Clark |
| 2004/0113847 A1 | 6/2004 | Qi et al. |
| 2004/0130425 A1 | 7/2004 | Dayan et al. |
| 2004/0130915 A1 | 7/2004 | Baarman |
| 2004/0130916 A1 | 7/2004 | Baarman |
| 2004/0142733 A1 | 7/2004 | Parise |
| 2004/0150934 A1 | 8/2004 | Baarman |
| 2004/0189246 A1 | 9/2004 | Bulai et al. |
| 2004/0201361 A1 | 10/2004 | Koh et al. |
| 2004/0222751 A1 | 11/2004 | Mollema et al. |
| 2004/0227057 A1 | 11/2004 | Tuominen et al. |
| 2004/0232845 A1 | 11/2004 | Baarman |
| 2004/0233043 A1 | 11/2004 | Yazawa et al. |
| 2004/0267501 A1 | 12/2004 | Freed et al. |
| 2005/0007067 A1 | 1/2005 | Baarman et al. |
| 2005/0021134 A1 | 1/2005 | Opie |
| 2005/0027192 A1 | 2/2005 | Govari et al. |
| 2005/0033382 A1 | 2/2005 | Single |
| 2005/0085873 A1 | 4/2005 | Gord et al. |
| 2005/0093475 A1 | 5/2005 | Kuennen et al. |
| 2005/0104064 A1 | 5/2005 | Hegarty et al. |
| 2005/0104453 A1 | 5/2005 | Vanderelli et al. |
| 2005/0116650 A1 | 6/2005 | Baarman |
| 2005/0116683 A1 | 6/2005 | Cheng et al. |
| 2005/0122058 A1 | 6/2005 | Baarman et al. |
| 2005/0122059 A1 | 6/2005 | Baarman et al. |
| 2005/0125093 A1 | 6/2005 | Kikuchi et al. |
| 2005/0127849 A1 | 6/2005 | Baarman et al. |
| 2005/0127850 A1 | 6/2005 | Baarman et al. |
| 2005/0127866 A1 | 6/2005 | Hamilton et al. |
| 2005/0135122 A1 | 6/2005 | Cheng et al. |
| 2005/0140482 A1 | 6/2005 | Cheng et al. |
| 2005/0151511 A1 | 7/2005 | Chary |
| 2005/0156560 A1 | 7/2005 | Shimaoka et al. |
| 2005/0189945 A1 | 9/2005 | Reiderman |
| 2005/0194926 A1 | 9/2005 | DiStefano |
| 2005/0253152 A1 | 11/2005 | Klimov et al. |
| 2005/0288739 A1 | 12/2005 | Hassler, Jr. et al. |
| 2005/0288740 A1 | 12/2005 | Hassler, Jr. et al. |
| 2005/0288741 A1 | 12/2005 | Hassler, Jr. et al. |
| 2005/0288742 A1 | 12/2005 | Giordano et al. |
| 2006/0001509 A1 | 1/2006 | Gibbs |
| 2006/0010902 A1 | 1/2006 | Trinh et al. |
| 2006/0022636 A1 | 2/2006 | Xian et al. |
| 2006/0053296 A1 | 3/2006 | Busboom et al. |
| 2006/0061323 A1 | 3/2006 | Cheng et al. |
| 2006/0066443 A1 | 3/2006 | Hall |
| 2006/0090956 A1 | 5/2006 | Peshkovskiy et al. |
| 2006/0132045 A1 | 6/2006 | Baarman |
| 2006/0164866 A1 | 7/2006 | Vanderelli et al. |
| 2006/0181242 A1 | 8/2006 | Freed et al. |
| 2006/0184209 A1 | 8/2006 | John et al. |
| 2006/0184210 A1 | 8/2006 | Singhal et al. |
| 2006/0185809 A1 | 8/2006 | Elfrink et al. |
| 2006/0199620 A1 | 9/2006 | Greene et al. |
| 2006/0202665 A1 | 9/2006 | Hsu |
| 2006/0205381 A1 | 9/2006 | Beart et al. |
| 2006/0214626 A1 | 9/2006 | Nilson et al. |
| 2006/0219448 A1 | 10/2006 | Grieve et al. |
| 2006/0238365 A1 | 10/2006 | Vecchione et al. |
| 2006/0270440 A1 | 11/2006 | Shearer et al. |
| 2006/0281435 A1 | 12/2006 | Shearer et al. |
| 2007/0010295 A1 | 1/2007 | Greene et al. |
| 2007/0013483 A1 | 1/2007 | Stewart |
| 2007/0016089 A1 | 1/2007 | Fischell et al. |
| 2007/0021140 A1 | 1/2007 | Keyes, IV et al. |
| 2007/0024246 A1 | 2/2007 | Flaugher |
| 2007/0064406 A1 | 3/2007 | Beart |
| 2007/0069687 A1 | 3/2007 | Suzuki |
| 2007/0096875 A1 | 5/2007 | Waterhouse et al. |
| 2007/0105429 A1 | 5/2007 | Kohl et al. |
| 2007/0117596 A1 | 5/2007 | Greene et al. |
| 2007/0126650 A1 | 6/2007 | Guenther |
| 2007/0145830 A1 | 6/2007 | Lee et al. |

(56) References Cited

U.S. PATENT DOCUMENTS

| | | |
|---|---|---|
| 2007/0164839 A1 | 7/2007 | Naito |
| 2007/0171681 A1 | 7/2007 | Baarman |
| 2007/0176840 A1 | 8/2007 | Pristas et al. |
| 2007/0178945 A1 | 8/2007 | Cook et al. |
| 2007/0182367 A1 | 8/2007 | Partovi |
| 2007/0208263 A1 | 9/2007 | John et al. |
| 2007/0222542 A1 | 9/2007 | Joannopoulos et al. |
| 2007/0257636 A1 | 11/2007 | Phillips et al. |
| 2007/0267918 A1 | 11/2007 | Gyland |
| 2007/0276538 A1 | 11/2007 | Kjellsson et al. |
| 2008/0012569 A1 | 1/2008 | Hall et al. |
| 2008/0014897 A1 | 1/2008 | Cook et al. |
| 2008/0030415 A1 | 2/2008 | Homan et al. |
| 2008/0036588 A1 | 2/2008 | Iverson et al. |
| 2008/0047727 A1 | 2/2008 | Sexton et al. |
| 2008/0051854 A1 | 2/2008 | Bulkes et al. |
| 2008/0067874 A1 | 3/2008 | Tseng |
| 2008/0132909 A1 | 6/2008 | Jascob et al. |
| 2008/0154331 A1 | 6/2008 | John et al. |
| 2008/0176521 A1 | 7/2008 | Singh et al. |
| 2008/0191638 A1 | 8/2008 | Kuennen et al. |
| 2008/0197710 A1 | 8/2008 | Kreitz et al. |
| 2008/0197802 A1 | 8/2008 | Onishi et al. |
| 2008/0211320 A1 | 9/2008 | Cook et al. |
| 2008/0238364 A1 | 10/2008 | Weber et al. |
| 2008/0255901 A1 | 10/2008 | Carroll et al. |
| 2008/0265684 A1 | 10/2008 | Farkas |
| 2008/0266748 A1 | 10/2008 | Lee |
| 2008/0272860 A1 | 11/2008 | Pance |
| 2008/0273242 A1 | 11/2008 | Woodgate et al. |
| 2008/0278264 A1 | 11/2008 | Karalis et al. |
| 2008/0291277 A1 | 11/2008 | Jacobsen et al. |
| 2008/0300657 A1 | 12/2008 | Stultz |
| 2008/0300660 A1 | 12/2008 | John |
| 2009/0010028 A1 | 1/2009 | Baarmen et al. |
| 2009/0015075 A1 | 1/2009 | Cook et al. |
| 2009/0033280 A1 | 2/2009 | Choi et al. |
| 2009/0033564 A1 | 2/2009 | Cook et al. |
| 2009/0038623 A1 | 2/2009 | Farbarik et al. |
| 2009/0045772 A1 | 2/2009 | Cook et al. |
| 2009/0051224 A1 | 2/2009 | Cook et al. |
| 2009/0058189 A1 | 3/2009 | Cook et al. |
| 2009/0058361 A1 | 3/2009 | John |
| 2009/0067198 A1 | 3/2009 | Graham et al. |
| 2009/0072627 A1 | 3/2009 | Cook et al. |
| 2009/0072628 A1 | 3/2009 | Cook et al. |
| 2009/0072629 A1 | 3/2009 | Cook et al. |
| 2009/0072782 A1 | 3/2009 | Randall |
| 2009/0079268 A1 | 3/2009 | Cook et al. |
| 2009/0079387 A1 | 3/2009 | Jin et al. |
| 2009/0085408 A1 | 4/2009 | Bruhn |
| 2009/0085706 A1 | 4/2009 | Baarman et al. |
| 2009/0096413 A1 | 4/2009 | Patovi et al. |
| 2009/0102292 A1 | 4/2009 | Cook et al. |
| 2009/0108679 A1 | 4/2009 | Porwal |
| 2009/0108997 A1 | 4/2009 | Patterson et al. |
| 2009/0115628 A1 | 5/2009 | Dicks et al. |
| 2009/0127937 A1 | 5/2009 | Widmer et al. |
| 2009/0134712 A1 | 5/2009 | Cook et al. |
| 2009/0146892 A1 | 6/2009 | Shimizu et al. |
| 2009/0153273 A1 | 6/2009 | Chen |
| 2009/0160261 A1 | 6/2009 | Elo |
| 2009/0161078 A1 | 6/2009 | Wu et al. |
| 2009/0167449 A1 | 7/2009 | Cook et al. |
| 2009/0174263 A1 | 7/2009 | Baarman et al. |
| 2009/0179502 A1 | 7/2009 | Cook et al. |
| 2009/0188396 A1 | 7/2009 | Hofmann et al. |
| 2009/0189458 A1 | 7/2009 | Kawasaki |
| 2009/0195332 A1 | 8/2009 | Joannopoulos et al. |
| 2009/0195333 A1 | 8/2009 | Joannopoulos et al. |
| 2009/0212636 A1 | 8/2009 | Cook et al. |
| 2009/0213028 A1 | 8/2009 | Cook et al. |
| 2009/0216292 A1* | 8/2009 | Pless et al. ............... 607/33 |
| 2009/0218884 A1 | 9/2009 | Soar |
| 2009/0224608 A1 | 9/2009 | Cook et al. |
| 2009/0224609 A1 | 9/2009 | Cook et al. |
| 2009/0224723 A1 | 9/2009 | Tanabe |
| 2009/0224856 A1 | 9/2009 | Karalis et al. |
| 2009/0230777 A1 | 9/2009 | Baarman et al. |
| 2009/0237194 A1 | 9/2009 | Waffenschmidt et al. |
| 2009/0243394 A1 | 10/2009 | Levine |
| 2009/0243397 A1 | 10/2009 | Cook et al. |
| 2009/0251008 A1 | 10/2009 | Sugaya |
| 2009/0261778 A1 | 10/2009 | Kook |
| 2009/0267558 A1 | 10/2009 | Jung |
| 2009/0267709 A1 | 10/2009 | Joannopoulos et al. |
| 2009/0267710 A1 | 10/2009 | Joannopoulos et al. |
| 2009/0271047 A1 | 10/2009 | Wakamatsu |
| 2009/0271048 A1 | 10/2009 | Wakamatsu |
| 2009/0273242 A1 | 11/2009 | Cook |
| 2009/0273318 A1 | 11/2009 | Rondoni et al. |
| 2009/0281678 A1 | 11/2009 | Wakamatsu |
| 2009/0284082 A1 | 11/2009 | Mohammadian |
| 2009/0284083 A1 | 11/2009 | Karalis et al. |
| 2009/0284218 A1 | 11/2009 | Mohammadian et al. |
| 2009/0284220 A1 | 11/2009 | Toncich et al. |
| 2009/0284227 A1 | 11/2009 | Mohammadian et al. |
| 2009/0284245 A1 | 11/2009 | Kirby et al. |
| 2009/0284369 A1 | 11/2009 | Toncich et al. |
| 2009/0286470 A1 | 11/2009 | Mohammadian et al. |
| 2009/0286475 A1 | 11/2009 | Toncich et al. |
| 2009/0286476 A1 | 11/2009 | Toncich et al. |
| 2009/0289595 A1 | 11/2009 | Chen et al. |
| 2009/0299918 A1 | 12/2009 | Cook et al. |
| 2009/0322158 A1 | 12/2009 | Stevens et al. |
| 2009/0322280 A1 | 12/2009 | Kamijo et al. |
| 2010/0015918 A1 | 1/2010 | Liu et al. |
| 2010/0017249 A1 | 1/2010 | Fincham et al. |
| 2010/0033021 A1 | 2/2010 | Bennett |
| 2010/0034238 A1 | 2/2010 | Bennett |
| 2010/0036773 A1 | 2/2010 | Bennett |
| 2010/0038970 A1 | 2/2010 | Cook et al. |
| 2010/0045114 A1 | 2/2010 | Sample et al. |
| 2010/0052431 A1 | 3/2010 | Mita |
| 2010/0052811 A1 | 3/2010 | Smith et al. |
| 2010/0060077 A1 | 3/2010 | Paulus et al. |
| 2010/0065352 A1 | 3/2010 | Ichikawa |
| 2010/0066349 A1 | 3/2010 | Lin et al. |
| 2010/0076524 A1 | 3/2010 | Forsberg et al. |
| 2010/0081379 A1 | 4/2010 | Cooper et al. |
| 2010/0094381 A1 | 4/2010 | Kim et al. |
| 2010/0096934 A1 | 4/2010 | Joannopoulos et al. |
| 2010/0102639 A1 | 4/2010 | Joannopoulos et al. |
| 2010/0102640 A1 | 4/2010 | Joannopoulos et al. |
| 2010/0102641 A1 | 4/2010 | Joannopoulos et al. |
| 2010/0104031 A1 | 4/2010 | Lacour |
| 2010/0109443 A1 | 5/2010 | Cook et al. |
| 2010/0109445 A1 | 5/2010 | Kurs et al. |
| 2010/0109604 A1 | 5/2010 | Boys et al. |
| 2010/0115474 A1 | 5/2010 | Takada et al. |
| 2010/0117454 A1 | 5/2010 | Cook et al. |
| 2010/0117455 A1 | 5/2010 | Joannopoulos et al. |
| 2010/0117456 A1 | 5/2010 | Karalis et al. |
| 2010/0117596 A1 | 5/2010 | Cook et al. |
| 2010/0123353 A1 | 5/2010 | Joannopoulos et al. |
| 2010/0123354 A1 | 5/2010 | Joannopoulos et al. |
| 2010/0123355 A1 | 5/2010 | Joannopoulos et al. |
| 2010/0123452 A1 | 5/2010 | Amano et al. |
| 2010/0123530 A1 | 5/2010 | Park et al. |
| 2010/0127573 A1 | 5/2010 | Joannopoulos et al. |
| 2010/0127574 A1 | 5/2010 | Joannopoulos et al. |
| 2010/0127575 A1 | 5/2010 | Joannopoulos et al. |
| 2010/0127660 A1 | 5/2010 | Cook et al. |
| 2010/0133918 A1 | 6/2010 | Joannopoulos et al. |
| 2010/0133919 A1 | 6/2010 | Joannopoulos et al. |
| 2010/0133920 A1 | 6/2010 | Joannopoulos et al. |
| 2010/0141042 A1 | 6/2010 | Kesler et al. |
| 2010/0148589 A1 | 6/2010 | Hamam et al. |
| 2010/0148723 A1 | 6/2010 | Cook et al. |
| 2010/0151808 A1 | 6/2010 | Toncich et al. |
| 2010/0156346 A1 | 6/2010 | Takada et al. |
| 2010/0156355 A1 | 6/2010 | Bauerle et al. |
| 2010/0156570 A1 | 6/2010 | Hong et al. |
| 2010/0164295 A1 | 7/2010 | Ichikawa et al. |

(56) References Cited

U.S. PATENT DOCUMENTS

| | | |
|---|---|---|
| 2010/0164296 A1 | 7/2010 | Kurs |
| 2010/0164297 A1 | 7/2010 | Kurs et al. |
| 2010/0164298 A1 | 7/2010 | Karalis et al. |
| 2010/0171368 A1 | 7/2010 | Schatz et al. |
| 2010/0171370 A1 | 7/2010 | Karalis et al. |
| 2010/0179384 A1 | 7/2010 | Hoeg et al. |
| 2010/0181843 A1 | 7/2010 | Schatz et al. |
| 2010/0181844 A1 | 7/2010 | Karalis et al. |
| 2010/0181845 A1 | 7/2010 | Fiorello et al. |
| 2010/0181961 A1 | 7/2010 | Novak et al. |
| 2010/0181964 A1 | 7/2010 | Huggins et al. |
| 2010/0184371 A1 | 7/2010 | Cook et al. |
| 2010/0187911 A1 | 7/2010 | Joannopoulos et al. |
| 2010/0187913 A1 | 7/2010 | Sample |
| 2010/0188183 A1 | 7/2010 | Shpiro |
| 2010/0190435 A1 | 7/2010 | Cook et al. |
| 2010/0190436 A1 | 7/2010 | Cook et al. |
| 2010/0194206 A1 | 8/2010 | Burdo et al. |
| 2010/0194207 A1 | 8/2010 | Graham |
| 2010/0194334 A1 | 8/2010 | Kirby et al. |
| 2010/0194335 A1 | 8/2010 | Kirby et al. |
| 2010/0201189 A1 | 8/2010 | Kirby et al. |
| 2010/0201201 A1 | 8/2010 | Mobarhan et al. |
| 2010/0201202 A1 | 8/2010 | Kirby et al. |
| 2010/0201203 A1 | 8/2010 | Schatz et al. |
| 2010/0201204 A1 | 8/2010 | Sakoda et al. |
| 2010/0201205 A1 | 8/2010 | Karalis et al. |
| 2010/0201310 A1 | 8/2010 | Vorenkamp et al. |
| 2010/0201312 A1 | 8/2010 | Kirby et al. |
| 2010/0201313 A1 | 8/2010 | Vorenkamp et al. |
| 2010/0201316 A1 | 8/2010 | Takada et al. |
| 2010/0201513 A1 | 8/2010 | Vorenkamp et al. |
| 2010/0207458 A1 | 8/2010 | Joannopoulos et al. |
| 2010/0210233 A1 | 8/2010 | Cook et al. |
| 2010/0213770 A1 | 8/2010 | Kikuchi |
| 2010/0213895 A1 | 8/2010 | Keating et al. |
| 2010/0217553 A1 | 8/2010 | Von Novak et al. |
| 2010/0219694 A1 | 9/2010 | Kurs et al. |
| 2010/0219695 A1 | 9/2010 | Komiyama et al. |
| 2010/0219696 A1 | 9/2010 | Kojima |
| 2010/0222010 A1 | 9/2010 | Ozaki et al. |
| 2010/0225175 A1 | 9/2010 | Karalis et al. |
| 2010/0225270 A1 | 9/2010 | Jacobs et al. |
| 2010/0225271 A1 | 9/2010 | Oyobe et al. |
| 2010/0225272 A1 | 9/2010 | Kirby et al. |
| 2010/0231053 A1 | 9/2010 | Karalis et al. |
| 2010/0231163 A1 | 9/2010 | Mashinsky |
| 2010/0231340 A1 | 9/2010 | Fiorello et al. |
| 2010/0234922 A1 | 9/2010 | Forsell |
| 2010/0235006 A1 | 9/2010 | Brown |
| 2010/0237706 A1 | 9/2010 | Karalis et al. |
| 2010/0237707 A1 | 9/2010 | Karalis et al. |
| 2010/0237708 A1 | 9/2010 | Karalis et al. |
| 2010/0237709 A1 | 9/2010 | Hall et al. |
| 2010/0244576 A1 | 9/2010 | Hillan et al. |
| 2010/0244577 A1 | 9/2010 | Shimokawa |
| 2010/0244578 A1 | 9/2010 | Yoshikawa |
| 2010/0244579 A1 | 9/2010 | Sogabe et al. |
| 2010/0244580 A1 | 9/2010 | Uchida et al. |
| 2010/0244581 A1 | 9/2010 | Uchida |
| 2010/0244582 A1 | 9/2010 | Yoshikawa |
| 2010/0244583 A1 | 9/2010 | Shimokawa |
| 2010/0244767 A1 | 9/2010 | Turner et al. |
| 2010/0244839 A1 | 9/2010 | Yoshikawa |
| 2010/0248622 A1 | 9/2010 | Lyell Kirby et al. |
| 2010/0253152 A1 | 10/2010 | Karalis et al. |
| 2010/0253281 A1 | 10/2010 | Li |
| 2010/0256481 A1 | 10/2010 | Mareci et al. |
| 2010/0256831 A1 | 10/2010 | Abramo et al. |
| 2010/0259108 A1 | 10/2010 | Giler et al. |
| 2010/0259109 A1 | 10/2010 | Sato |
| 2010/0259110 A1 | 10/2010 | Kurs et al. |
| 2010/0264745 A1 | 10/2010 | Karalis et al. |
| 2010/0264746 A1 | 10/2010 | Kazama et al. |
| 2010/0264747 A1 | 10/2010 | Hall et al. |
| 2010/0276995 A1 | 11/2010 | Marzetta et al. |
| 2010/0277003 A1 | 11/2010 | Von Novak et al. |
| 2010/0277004 A1 | 11/2010 | Suzuki et al. |
| 2010/0277005 A1 | 11/2010 | Karalis et al. |
| 2010/0277120 A1 | 11/2010 | Cook et al. |
| 2010/0277121 A1 | 11/2010 | Hall et al. |
| 2010/0289341 A1 | 11/2010 | Ozaki et al. |
| 2010/0289449 A1 | 11/2010 | Elo |
| 2010/0295505 A1 | 11/2010 | Jung et al. |
| 2010/0295506 A1 | 11/2010 | Ichikawa |
| 2010/0308939 A1 | 12/2010 | Kurs |
| 2010/0314946 A1 | 12/2010 | Budde et al. |
| 2010/0327660 A1 | 12/2010 | Karalis et al. |
| 2010/0327661 A1 | 12/2010 | Karalis et al. |
| 2010/0328044 A1 | 12/2010 | Waffenschmidt et al. |
| 2011/0004269 A1 | 1/2011 | Strother et al. |
| 2011/0012431 A1 | 1/2011 | Karalis et al. |
| 2011/0018361 A1 | 1/2011 | Karalis et al. |
| 2011/0025131 A1 | 2/2011 | Karalis et al. |
| 2011/0031928 A1 | 2/2011 | Soar |
| 2011/0043046 A1 | 2/2011 | Joannopoulos et al. |
| 2011/0043047 A1 | 2/2011 | Karalis et al. |
| 2011/0043048 A1 | 2/2011 | Karalis et al. |
| 2011/0043049 A1 | 2/2011 | Karalis et al. |
| 2011/0049995 A1 | 3/2011 | Hashiguchi |
| 2011/0049996 A1 | 3/2011 | Karalis et al. |
| 2011/0049998 A1 | 3/2011 | Karalis et al. |
| 2011/0074218 A1 | 3/2011 | Karalis et al. |
| 2011/0074346 A1 | 3/2011 | Hall et al. |
| 2011/0074347 A1 | 3/2011 | Karalis et al. |
| 2011/0089895 A1 | 4/2011 | Karalis et al. |
| 2011/0095618 A1 | 4/2011 | Schatz et al. |
| 2011/0115303 A1 | 5/2011 | Baarman et al. |
| 2011/0115431 A1 | 5/2011 | Dunworth et al. |
| 2011/0121920 A1 | 5/2011 | Kurs et al. |
| 2011/0128015 A1 | 6/2011 | Dorairaj et al. |
| 2011/0140544 A1 | 6/2011 | Karalis et al. |
| 2011/0148219 A1 | 6/2011 | Karalis et al. |
| 2011/0162895 A1 | 7/2011 | Karalis et al. |
| 2011/0169339 A1 | 7/2011 | Karalis et al. |
| 2011/0181122 A1 | 7/2011 | Karalis et al. |
| 2011/0193416 A1 | 8/2011 | Campanella et al. |
| 2011/0193419 A1 | 8/2011 | Karalis et al. |
| 2011/0198939 A1 | 8/2011 | Karalis et al. |
| 2011/0215086 A1 | 9/2011 | Yeh |
| 2011/0221278 A1 | 9/2011 | Karalis et al. |
| 2011/0227528 A1 | 9/2011 | Karalis et al. |
| 2011/0227530 A1 | 9/2011 | Karalis et al. |
| 2011/0241618 A1 | 10/2011 | Karalis et al. |
| 2011/0248573 A1 | 10/2011 | Kanno et al. |
| 2011/0254377 A1 | 10/2011 | Wildmer et al. |
| 2011/0254503 A1 | 10/2011 | Widmer et al. |
| 2011/0266878 A9 | 11/2011 | Cook et al. |
| 2011/0278943 A1 | 11/2011 | Eckhoff et al. |
| 2012/0001492 A9 | 1/2012 | Cook et al. |
| 2012/0001593 A1 | 1/2012 | DiGuardo |
| 2012/0007435 A1 | 1/2012 | Sada et al. |
| 2012/0007441 A1 | 1/2012 | John et al. |
| 2012/0025602 A1 | 2/2012 | Boys et al. |
| 2012/0032522 A1 | 2/2012 | Schatz et al. |
| 2012/0038525 A1 | 2/2012 | Monsalve Carcelen et al. |
| 2012/0062345 A1 | 3/2012 | Kurs et al. |
| 2012/0068549 A1 | 3/2012 | Karalis et al. |
| 2012/0086284 A1 | 4/2012 | Capanella et al. |
| 2012/0086867 A1 | 4/2012 | Kesler et al. |
| 2012/0091794 A1 | 4/2012 | Campanella et al. |
| 2012/0091795 A1 | 4/2012 | Fiorello et al. |
| 2012/0091796 A1 | 4/2012 | Kesler et al. |
| 2012/0091797 A1 | 4/2012 | Kesler et al. |
| 2012/0091819 A1 | 4/2012 | Kulikowski et al. |
| 2012/0091820 A1 | 4/2012 | Campanella et al. |
| 2012/0091949 A1 | 4/2012 | Campanella et al. |
| 2012/0091950 A1 | 4/2012 | Campanella et al. |
| 2012/0098350 A1 | 4/2012 | Campanella et al. |
| 2012/0112531 A1 | 5/2012 | Kesler et al. |
| 2012/0112532 A1 | 5/2012 | Kesler et al. |
| 2012/0112534 A1 | 5/2012 | Kesler et al. |
| 2012/0112535 A1 | 5/2012 | Karalis et al. |
| 2012/0112536 A1 | 5/2012 | Karalis et al. |

(56) References Cited

U.S. PATENT DOCUMENTS

| | | | |
|---|---|---|---|
| 2012/0112538 A1 | 5/2012 | Kesler et al. | |
| 2012/0112691 A1 | 5/2012 | Kurs et al. | |
| 2012/0119569 A1 | 5/2012 | Karalis et al. | |
| 2012/0119575 A1 | 5/2012 | Kurs et al. | |
| 2012/0119576 A1 | 5/2012 | Kesler et al. | |
| 2012/0119698 A1 | 5/2012 | Karalis et al. | |
| 2012/0139355 A1 | 6/2012 | Ganem et al. | |
| 2012/0146575 A1 | 6/2012 | Armstrong et al. | |
| 2012/0153732 A1 | 6/2012 | Kurs et al. | |
| 2012/0153733 A1 | 6/2012 | Schatz et al. | |
| 2012/0153734 A1 | 6/2012 | Kurs et al. | |
| 2012/0153735 A1 | 6/2012 | Karalis et al. | |
| 2012/0153736 A1 | 6/2012 | Karalis et al. | |
| 2012/0153737 A1 | 6/2012 | Karalis et al. | |
| 2012/0153738 A1 | 6/2012 | Karalis et al. | |
| 2012/0153893 A1 | 6/2012 | Schatz et al. | |
| 2012/0184338 A1 | 7/2012 | Kesler et al. | |
| 2012/0206096 A1 | 8/2012 | John | |
| 2012/0223573 A1 | 9/2012 | Schatz et al. | |
| 2012/0228952 A1 | 9/2012 | Hall et al. | |
| 2012/0228953 A1 | 9/2012 | Kesler et al. | |
| 2012/0228954 A1 | 9/2012 | Kesler et al. | |
| 2012/0235500 A1 | 9/2012 | Kesler et al. | |
| 2012/0235501 A1 | 9/2012 | Kesler et al. | |
| 2012/0235502 A1 | 9/2012 | Kesler et al. | |
| 2012/0235503 A1 | 9/2012 | Kesler et al. | |
| 2012/0235504 A1 | 9/2012 | Kesler et al. | |
| 2012/0235505 A1 | 9/2012 | Schatz et al. | |
| 2012/0235566 A1 | 9/2012 | Karalis et al. | |
| 2012/0235567 A1 | 9/2012 | Karalis et al. | |
| 2012/0235633 A1 | 9/2012 | Kesler et al. | |
| 2012/0235634 A1 | 9/2012 | Hall et al. | |
| 2012/0239117 A1 | 9/2012 | Kesler et al. | |
| 2012/0242159 A1 | 9/2012 | Lou et al. | |
| 2012/0242225 A1 | 9/2012 | Karalis et al. | |
| 2012/0248884 A1 | 10/2012 | Karalis et al. | |
| 2012/0248886 A1 | 10/2012 | Kesler et al. | |
| 2012/0248887 A1 | 10/2012 | Kesler et al. | |
| 2012/0248888 A1 | 10/2012 | Kesler et al. | |
| 2012/0248981 A1 | 10/2012 | Karalis et al. | |
| 2012/0256494 A1 | 10/2012 | Kesler et al. | |
| 2012/0267960 A1 | 10/2012 | Low et al. | |
| 2012/0280765 A1 | 11/2012 | Kurs et al. | |
| 2012/0313449 A1 | 12/2012 | Kurs et al. | |
| 2012/0313742 A1 | 12/2012 | Kurs et al. | |
| 2013/0007949 A1 | 1/2013 | Kurs et al. | |
| 2013/0020878 A1 | 1/2013 | Karalis et al. | |
| 2013/0033118 A1 | 2/2013 | Karalis et al. | |
| 2013/0038402 A1 | 2/2013 | Karalis et al. | |
| 2013/0057364 A1 | 3/2013 | Kesler et al. | |
| 2013/0062966 A1 | 3/2013 | Verghese et al. | |
| 2013/0069441 A1 | 3/2013 | Verghese et al. | |
| 2013/0069753 A1 | 3/2013 | Kurs et al. | |
| 2013/0099587 A1 | 4/2013 | Lou | |
| 2013/0154383 A1 | 6/2013 | Kasturi et al. | |
| 2013/0154389 A1 | 6/2013 | Kurs et al. | |
| 2013/0159956 A1 | 6/2013 | Verghese et al. | |
| 2013/0175874 A1 | 7/2013 | Lou et al. | |
| 2013/0175875 A1 | 7/2013 | Kurs et al. | |
| 2013/0198463 A1* | 8/2013 | Hintz | 711/154 |
| 2013/0200716 A1 | 8/2013 | Kesler et al. | |
| 2013/0200721 A1 | 8/2013 | Kurs et al. | |
| 2013/0221744 A1 | 8/2013 | Hall et al. | |
| 2013/0278073 A1 | 10/2013 | Kurs et al. | |
| 2013/0278074 A1 | 10/2013 | Kurs et al. | |
| 2013/0278075 A1 | 10/2013 | Kurs et al. | |
| 2013/0300353 A1 | 11/2013 | Kurs et al. | |
| 2013/0307349 A1 | 11/2013 | Hall et al. | |
| 2013/0320773 A1 | 12/2013 | Schatz et al. | |
| 2013/0334892 A1 | 12/2013 | Hall et al. | |
| 2014/0002012 A1 | 1/2014 | McCauley et al. | |
| 2014/0070764 A1 | 3/2014 | Keeling | |
| 2014/0191724 A1* | 7/2014 | Wojcik et al. | 320/114 |

FOREIGN PATENT DOCUMENTS

| | | |
|---|---|---|
| CN | 102439669 | 5/2012 |
| CN | 103329397 | 9/2013 |
| DE | 38 24 972 | 1/1989 |
| DE | 100 29147 | 12/2001 |
| DE | 200 16 655 | 3/2002 |
| DE | 102 21 484 | 11/2003 |
| DE | 103 04 584 | 8/2004 |
| DE | 10 2005 036290 | 2/2007 |
| DE | 10 2006 044057 | 4/2008 |
| EP | 1 335 477 | 8/2003 |
| EP | 1 521 206 | 4/2005 |
| EP | 1 524 010 | 4/2005 |
| EP | 2 357 716 | 8/2011 |
| JP | 02-097005 | 4/1990 |
| JP | 4-265875 | 9/1992 |
| JP | 6-341410 | 12/1994 |
| JP | 9-182323 | 7/1997 |
| JP | 9-298847 | 11/1997 |
| JP | 10-164837 | 6/1998 |
| JP | 11-75329 | 3/1999 |
| JP | 11-188113 | 7/1999 |
| JP | 2001-309580 | 11/2001 |
| JP | 2002-010535 | 1/2002 |
| JP | 2003-179526 | 6/2003 |
| JP | 2004-166459 | 6/2004 |
| JP | 2004-201458 | 7/2004 |
| JP | 2004-229144 | 8/2004 |
| JP | 2005-57444 | 3/2005 |
| JP | 2005-149238 | 6/2005 |
| JP | 2006-074848 | 3/2006 |
| JP | 2007-505480 | 3/2007 |
| JP | 2007-266892 | 10/2007 |
| JP | 2007-537637 | 12/2007 |
| JP | 2008-508842 | 3/2008 |
| JP | 2008-206231 | 9/2008 |
| JP | 2008-206327 | 9/2008 |
| JP | 2011-072074 | 4/2011 |
| JP | 2012-504387 | 2/2012 |
| JP | 2013-543718 | 12/2013 |
| KR | 10-2007-0017804 | 2/2007 |
| KR | 10-2008-0007635 | 1/2008 |
| KR | 10-2009-0122072 | 11/2009 |
| KR | 10-2011-0050920 | 5/2011 |
| SG | 112842 | 7/2005 |
| WO | WO 92/17929 | 10/1992 |
| WO | WO 93/23908 | 11/1993 |
| WO | WO 94/28560 | 12/1994 |
| WO | WO 95/11545 | 4/1995 |
| WO | WO 96/02970 | 2/1996 |
| WO | WO 98/50993 | 11/1998 |
| WO | WO 00/77910 | 12/2000 |
| WO | WO 03/092329 | 11/2003 |
| WO | WO 03/096361 | 11/2003 |
| WO | WO 03/096512 | 11/2003 |
| WO | WO 2004/015885 | 2/2004 |
| WO | WO 2004/038888 | 5/2004 |
| WO | WO 2004/055654 | 7/2004 |
| WO | WO 2004/073150 | 8/2004 |
| WO | WO 2004/073166 | 8/2004 |
| WO | WO 2004/073176 | 8/2004 |
| WO | WO 2004/073177 | 8/2004 |
| WO | WO 2004/112216 | 12/2004 |
| WO | WO 2005/024865 | 3/2005 |
| WO | WO 2005/060068 | 6/2005 |
| WO | WO 2005/109597 | 11/2005 |
| WO | WO 2005/109598 | 11/2005 |
| WO | WO 2006/011769 | 2/2006 |
| WO | WO 2007/008646 | 1/2007 |
| WO | WO 2007/020583 | 2/2007 |
| WO | WO 2007/042952 | 4/2007 |
| WO | WO 2007/084716 | 7/2007 |
| WO | WO 2007/084717 | 7/2007 |
| WO | WO 2008/109489 | 9/2008 |
| WO | WO 2008/118178 | 10/2008 |
| WO | WO 2009/009559 | 1/2009 |
| WO | WO 2009/018568 | 2/2009 |
| WO | WO 2009/023155 | 2/2009 |

(56) References Cited

FOREIGN PATENT DOCUMENTS

| WO | WO 2009/023646 | 2/2009 |
|---|---|---|
| WO | WO 2009/033043 | 3/2009 |
| WO | WO 2009/062438 | 5/2009 |
| WO | WO 2009/070730 | 6/2009 |
| WO | WO 2009/126963 | 10/2009 |
| WO | WO 2009/140506 | 11/2009 |
| WO | WO 2009/149464 | 12/2009 |
| WO | WO 2009/155000 | 12/2009 |
| WO | WO 2010/030977 | 3/2010 |
| WO | WO 2010/036980 | 4/2010 |
| WO | WO 2010/039967 | 4/2010 |
| WO | WO 2010/090538 | 8/2010 |
| WO | WO 2010/090539 | 8/2010 |
| WO | WO 2010/093997 | 8/2010 |
| WO | WO 2010/104569 | 9/2010 |
| WO | WO 2011/061388 | 5/2011 |
| WO | WO 2011/061821 | 5/2011 |
| WO | WO 2011/062827 | 5/2011 |
| WO | WO 2011/112795 | 9/2011 |
| WO | WO 2012/037279 | 3/2012 |
| WO | WO 2012/170278 | 12/2012 |
| WO | WO 2013/013235 | 1/2013 |
| WO | WO 2013/020138 | 2/2013 |
| WO | WO 2013/036947 | 3/2013 |
| WO | WO 2013/059441 | 4/2013 |
| WO | WO 2013/067484 | 5/2013 |
| WO | WO 2013/113017 | 8/2013 |
| WO | WO 2013/142840 | 9/2013 |
| WO | WO 2014/004843 | 1/2014 |

OTHER PUBLICATIONS

"Physics Update, Unwired Energy", *Physics Today*, pp. 26, (Jan. 2007) (See http://arxiv.org/abs/physics/0611063.).
"In pictures: A year in technology", *BBC News*, (Dec. 28, 2007).
"Next Little Thing 2010 Electricity without wires", CNN Money (See money.cnn.com/galleries/2009/smallbusiness/0911/gallery.next_little_thing_2010.smb/) (dated Nov. 30, 2009).
Abe et al. "A Noncontact Charger Using a Resonant Converter with Parallel Capacitor of the Secondary Coil". IEEE, 36(2):444-451, Mar./Apr. 2000.
Ahmadian, M. et al., "Miniature Transmitter for Implantable Micro Systems", *Proceedings of the 25th Annual International Conference of the IEEE EMBS* Cancun, Mexico, pp. 3028-3031 (Sep. 17-21, 2003).
Aoki, T. et al., "Observation of strong coupling between one atom and a monolithic microresonator", Nature, vol. 443:671-674 (2006).
Apneseth et al. "Introducing wireless proximity switches" ABB Review Apr. 2002.
Aristeidis Karalis et al., "Efficient Wireless *non-radiative mid-range* energy transfer", *Annals of Physics*, vol. 323, pp. 34-48 (2008).
Baker et al., "Feedback Analysis and Design of RF Power Links for Low-Power Bionic Systems," *IEEE Transactions on Biomedical Circuits and Systems*, vol. 1(1):28-38 (Mar. 2007).
Balanis, C.A., "Antenna Theory: Analysis and Design," 3rd Edition, Sections 4.2, 4.3, 5.2, 5.3 (Wiley, New Jersey, 2005).
Berardelli, P., "Outlets Are Out", ScienceNOW Daily News, Science Now, http://sciencenow.sciencemag.org/ cgi/content/full/2006/1114/2, (Nov. 14, 2006) 2 pages.
Biever, C., "Evanescent coupling' could power gadgets wirelessly", NewScientistsTech.com, http://www. newscientisttech.com/article.ns?id=dn1 0575&print=true, (Nov. 15, 2006) 2 pages.
Borenstein, S., "Man tries wirelessly boosting batteries", (The Associated Press), USA Today, (Nov. 16, 2006) 1 page.
Borenstein, S., "Man tries wirelessly boosting batteries", AP Science Writer, Boston.com, (See http://www.boston.com/business/technology/articles/2006/11/15/man_tries_wirelessly_b . . . ) (Nov. 15, 2006).
Boyle, A., "Electro-nirvana? Not so fast", MSNBC, http:/lcosmiclog.msnbc.msn.com/_news/2007/06/08/4350760- electro-nirvana-not-so-fast, (Jun. 8, 2007) 1 page.

Budhia, M. et al., "A New IPT Magnetic Coupler for Electric Vehicle Charging Systems", IECON 2010—36th Annual Conference on IEEE Industrial Electronics Society, Glendale, AZ, pp. 2487-2492 (Nov. 7-10, 2010).
Budhia, M. et al., "Development and evaluation of single sided flux couplers for contactless electric vehicle charging", 2011 IEEE Energy Conversion Congress and Exposition (ECCE), Phoenix, AZ, pp. 614-621 (Sep. 17-22, 2011).
Budhia, M. et al.,"Development of a Single-Sided Flux Magnetic Coupler for Electric Vehicle IPT", *IEEE Transactions on Industrial Electronics*, vol. 60:318-328 (Jan. 2013).
Bulkeley, W. M., "MIT Scientists Pave the Way for Wireless Battery Charging", The Wall Street Journal (See http://online.wsj.com/article/SB118123955549228045.html?mod=googlenews_wsj), (Jun. 8, 2007) 2 pages.
Burri et al., "Invention Description", (Feb. 5, 2008).
Cass, S., "Air Power—Wireless data connections are common—now scientists are working on wireless power", Sponsored by IEEE Spectrum, http://spectrum.ieee.org/computing/hardware/air-power, (Nov. 2006) 2 pages.
Castelvecchi, Davide, "The Power of Induction—Cutting the last cord could resonate with our increasingly gadget dependent lives", *Science News Online*, vol. 172, No. 3, Jul. 21, 2007, 6 pages.
Chang, A., "Recharging the Wireless Way—Even physicists forget to recharge their cell phones sometimes.", PC Magazine, ABC News Internet Ventures, (Dec. 12, 2006) 1 page.
Chinaview, ,"Scientists light bulb with 'wireless electricity'",www.Chinaview.cn, http://news.xinhuanet.com/english/2007-06/08/content_6215681.htm,Jun. 2007,1 page.
Cooks, G., "The vision of an MIT physicist: Getting rid of pesky rechargers", Boston.com, (Dec. 11, 2006) 1 page.
Derbyshire, D., "The end of the plug? Scientists invent wireless device that beams electricity through your home", Daily Mail, http://www.dailymail.co.uk/pages/live/articles/technology/technology.html?in_article_id=4 . . . ), (Jun. 7, 2007) 3 pages.
Eisenberg, Anne, "Automatic Recharging, From a Distance", The New York Times, (see www.nytimes.com/2012/03/11/business/built-in-wireless-chargeing-for-electronic-devices.html?_r=0) (published on Mar. 10, 2012).
Esser et al., "A New Approach to Power Supplies for Robots", IEEE, vol. 27(5):872-875, (Sep./Oct. 1991).
Fan, Shanhui et al., "Rate-Equation Analysis of Output Efficiency and Modulation Rate of Photomic-Crystal Light-Emitting Diodes", IEEE Journal of Quantum Electronics, vol. 36(10):1123-1130 (Oct. 2000).
Fenske et al., "Dielectric Materials at Microwave Frequencies", Applied Microwave & Wireless, pp. 92-100 (2000).
Fernandez, C. et al., "A simple dc-dc converter for the power supply of a cochlear implant", *IEEE*, pp. 1965-1970 (2003).
Ferris, David, "How Wireless Charging Will Make Life Simpler (and Greener)", Forbes (See forbes.com/sites/davidferris/2012/07/24/how-wireless-charging-will-make-life-simpler-and-greener/print/) (dated Jul. 24, 2012).
Fildes, J., "Physics Promises Wireless Power", (Science and Technology Reporter), BBC News, (Nov. 15, 2006) 3 pages.
Fildes, J., "The technology with impact 2007", BBC News, (Dec. 27, 2007) 3 pages.
Fildes, J., "Wireless energy promise powers up", BBC News, http://news.bbc.co.uk/2/hi/technology/6725955.stm, (Jun. 7, 2007) 3 pages.
Finkenzeller, Klaus, "RFID Handbook—Fundamentals and Applications in Contactless Smart Cards", Nikkan Kohgyo-sya, Kanno Taihei, first version, pp. 32-37, 253 (Aug. 21, 2001).
Finkenzeller, Klaus, "RFID Handbook (2nd Edition)", The Nikkan Kogyo Shimbun, Ltd., pp. 19, 20, 38, 39, 43, 44, 62, 63, 67, 68, 87, 88, 291, 292 (Published on May 31, 2004).
Freedman, D.H., "Power on a Chip", MIT Technology Review, (Nov. 2004).
Gary Peterson, "MIT WiTricity Not So Original After All", *Feed Line No. 9*, (See http://www.tfcbooks.com/articles/witricity.htm) printed Nov. 12, 2009.

(56) References Cited

OTHER PUBLICATIONS

Geyi, Wen, "A Method for the Evaluation of Small Antenna Q", IEEE Transactions on Antennas and Propagation, vol. 51(8):2124-2129 (Aug. 2003).
Hadley, F., "Goodbye Wires—MIT Team Experimentally Demonstrates Wireless Power Transfer, Potentially Useful for Power Laptops, Cell-Phones Without Cords", Massachusetts Institute of Technology, Institute for Soldier D Nanotechnologies, http://web.mit.edu/newsoffice/2007/wireless-0607.html, (Jun. 7, 2007) 3 pages.
Haus, H.A., "Waves and Fields in Optoelectronics," Chapter 7 "Coupling of Modes—Reasonators and Couplers" (Prentice-Hall, New Jersey, 1984).
Heikkinen et al., "Performance and Efficiency of Planar Rectennas for Short-Range Wireless Power Transfer at 2.45 GHz", Microwave and Optical Technology Letters, vol. 31(2):86-91, (Oct. 20, 2001).
Highfield, R., "Wireless revolution could spell end of plugs",(Science Editor), Telegraph.co.uk, http://www. telegraph.co.uk/news/main.jhtml?xml=/news/2007/06/07/nwireless1 07.xml, (Jun. 7, 2007) 3 pages.
Hirai et al., "Integral Motor with Driver and Wireless Transmission of Power and Information for Autonomous Subspindle Drive", IEEE, vol. 15(1):13-20, (Jan. 2000).
Hirai et al., "Practical Study on Wireless Transmission of Power and Information for Autonomous Decentralized Manufacturing System", IEEE, vol. 46(2):349-359, Apr. 1999.
Hirai et al., "Study on Intelligent Battery Charging Using Inductive Transmission of Power and Information", IEEE, vol. 15(2):335-345, (Mar. 2000).
Hirai et al., "Wireless Transmission of Power and Information and Information for Cableless Linear Motor Drive", IEEE, vol. 15(1):21-27, (Jan. 2000).
Hirayama, M., "Splashpower—World Leaders in Wireless Power", PowerPoint presentation, Splashpower Japan, (Sep. 3, 2007) 30 pages.
Ho, S. L. et al., "A Comparative Study Between Novel Witricity and Traditional Inductive Magnetic Coupling in Wireless Charging", IEEE Transactions on Magnetics, vol. 47(5):1522-1525 (May 2011).
Infotech Online, "Recharging gadgets without cables", infotech.indiatimes.com, (Nov. 17, 2006) 1 page.
Jackson, J. D., "Classical Electrodynamics", 3rd Edition, Wiley, New York, 1999, pp. 201-203.
Jackson, J.D., "Classical Electrodynamics," 3rd Edition, Sections 1.11, 5.5, 5.17, 6.9, 8.1, 8.8, 9.2, 9.3 (Wiley, New York, 1999).
Jacob, M. V. et al., "Lithium Tantalate—A High Permittivity Dielectric Material for Microwave Communication Systems", *Proceedings of IEEE TENCON—Poster Papers*, pp. 1362-1366, 2003.
Karalis, Aristeidis, "Electricity Unplugged", Feature: Wireless Energy Physics World, physicsworld.com, pp. 23-25 (Feb. 2009).
Kawamura et al., "Wireless Transmission of Power and Information Through One High-Frequency Resonant AC Link Inverter for Robot Manipulator Applications", IEEE, vol. 32(3):503-508, (May/Jun. 1996).
Kurs, A. et al., "Wireless Power Transfer via Strongly Coupled Magnetic Resonances", *Science*, vol. 317, pp. 83-86 (Jul. 6, 2007).
Kurs, A. et al., "Simultaneous mid-range power transfer to multiple devices", *Applied Physics Letters*, vol. 96, No. 044102 (2010).
Kurs, A. et al.,"Optimized design of a low-resistance electrical conductor for the multimegahertz range", *Applied Physics Letters*, vol. 98:172504-172504-3 (Apr. 2011).
Lamb, Gregory M. ,"Look Ma—no wires!—Electricity broadcast through the air may someday run your home",The Christian Science Monitor,http://www.csmonitor.com/2006/1116/p14s01-stct.html,Nov. 15, 2006,2 pages.
Lee, "Antenna Circuit Design for RFID Applications," Microchip Technology Inc., AN710, 50 pages (2003).
Lee, "RFID Coil Design," Microchip Technology Inc., AN678, 21 pages (1998).
Liang et al., "Silicon waveguide two-photon absorption detector at 1.5 µm wavelength for autocorrelation measurements," Applied Physics Letters, 81(7):1323-1325 (Aug. 12, 2002).
Markoff, J. ,"Intel Moves to Free Gadgets of Their Recharging Cords", The New York Times—nytimes.com, Aug. 21, 2008, 2 pages.
Mediano, A. et al. "Design of class E amplifier with nonlinear and linear shunt capacitances for any duty cycle", IEEE Trans. Microwave Theor. Tech., vol. 55, No. 3, pp. 484-492, (2007).
Microchip Technology Inc., "microID 13.56 MHz Design Guide— MCRF355/360 Reader Reference Design," 24 pages (2001).
Minkel, J R. ,"Wireless Energy Lights Bulb from Seven Feet Away— Physicists vow to cut the cord between your laptop battery and the wall socket—with just a simple loop of wire",Scientific American,http://www.scientificamerican.com/article.cfm?id=wireless-energy-lights-bulb-from-seven-feet-away,Jun. 7, 2007,1 page.
Minkel, J R. ,"Wireless Energy Transfer May Power Devices at a Distance",Scientific American,Nov. 14, 2006,1 page.
Morgan, J., "Lab report: Pull the plug for a positive charge", The Herald, Web Issue 2680, (Nov. 16, 2006) 3 pages.
Moskvitch, Katia, "Wireless charging—the future for electric cars?", BBC News Technology (See www.bbc.co.uk/news/technology-14183409) (dated Jul. 21, 2011).
O'Brien et al., "Analysis of Wireless Power Supplies for Industrial Automation Systems", IEEE, pp. 367-372 (Nov. 2-6, 2003).
O'Brien et al., "Design of Large Air-Gap Transformers for Wireless Power Supplies", IEEE, pp. 1557-1562 (Jun. 15-19, 2003).
Pendry, J. B., "A Chiral Route to Negative Refraction", Science, vol. 306:1353-1355 (2004).
Physics Today, "Unwired energy questions asked answered", Sep. 2007, pp. 16-17.
Powercast LLC. "White Paper" Powercast simply wire free, 2003.
PR News Wire, "The Big Story for CES 2007: The public debut of eCoupled Intelligent Wireless Power", Press Release, Fulton Innovation LLC, Las Vegas, NV, (Dec. 27, 2006) 3 pages.
Press Release, "The world's first sheet-type wireless power transmission system: Will a socket be replaced by e-wall?",Public Relations Office, School of Engineering, University of Tokyo, Japan,Dec. 12, 2006,4 pages.
PRESSTV, "Wireless power transfer possible", http://edition.presstv.ir/detail/12754.html, Jun. 11, 2007, 1 page.
Reidy, C. (Globe Staff), "MIT discovery could unplug your iPod forever", Boston.com, http://www.boston.com/ business/ticker/2007/06/mit_discovery_c.html, (Jun. 7, 2007) 3 pages.
Risen, C., "Wireless Energy", The New York Times, (Dec. 9, 2007) 1 page.
Sakamoto et al., "A Novel Circuit for Non-Contact Charging Through Electro-Magnetic Coupling", IEEE, pp. 168-174 (1992).
Scheible, G. et al., "Novel Wireless Power Supply System for Wireless Communication Devices in Industrial Automation Systems", IEEE, pp. 1358-1363, (Nov. 5-8, 2002).
Schneider, D. "A Critical Look at Wireless Power", *IEEE Spectrum*, pp. 35-39 (May 2010).
Schneider, David, "Electrons Unplugged. Wireless power at a distance is still far away", *IEEE Spectrum*, pp. 35-39 (May 2010).
Schuder, J. C. et al., "An Inductively Coupled RF System for the Transmission of 1 kW of Power Through the Skin", *IEEE Transactions on Bio-Medical Engineering*, vol. BME-18, No. 4, pp. 265-273 (Jul. 1971).
Schuder, J. C., "Powering an Artificial Heart: Birth of the Inductively Coupled-Radio Frequency System in 1960", *Artificial Organs*, vol. 26:909-915 (2002).
Schuder, J.C. et al., "Energy Transport Into the Closed Chest From a Set of Very-Large Mutually Orthogonal Coils", Communication Electronics, vol. 64:527-534 (Jan. 1963).
Schutz, J. et al., "Load Adaptive Medium Frequency Resonant Power Supply", IEEE, pp. 282-287 (Nov. 2002).
Sekitani et al. "A large-area wireless power-transmission sheet using printed organic transistors and plastic MEMS switches" www.nature.com/naturematerials. Published online Apr. 29, 2007.
Sekitani et al., "A large-area flexible wireless power transmission sheet using printed plastic MEMS switches and organic field-effect transistors", IEDM '06, International Electron Devices Meeting, (Dec. 11-13, 2006) 4 pages.
Sekiya, H. et al., "FM/PWM control scheme in class DE inverter", IEEE Trans. Circuits Syst. I, vol. 51(7) (Jul. 2004).

(56) References Cited

OTHER PUBLICATIONS

Senge, M., "MIT's wireless electricity for mobile phones", Vanguard, http://www.vanguardngr.com/articles/2002/features/gsm/gsm211062007.htm, (Jun. 11, 2007) 1 page.
Sensiper, S., "Electromagnetic wave propogation on helical conductors", Technical Report No. 194 (based on PhD Thesis), Massachusetts Institute of Technology, (May 16, 1951) 126 pages.
Soljacic, M., "Wireless Non-Radiative Energy Transfer—PowerPoint presentation". Massachusetts Institute of Technology, (Oct. 6, 2005).
Soljacic, M. et al., "Wireless Energy Transfer Can Potentially Recharge Laptops Cell Phones Without Cords", (Nov. 14, 2006) 3 pages.
Soljacic, M. et al., "Photonic-crystal slow-light enhancement of non-linear phase sensitivity", *J. Opt. Soc. Am B*, vol. 19, No. 9, pp. 2052-2059 (Sep. 2002).
Soljacic, M., "Wireless nonradiative energy transfer", *Visions of Discovery New Light on Physics, Cosmology, and Consciousness*, Cambridge University Press, New York, NY pp. 530-542 (2011).
Someya, Takao. "The world's first sheet-type wireless power transmission system". University of Tokyo, (Dec. 12, 2006).
Staelin, David H. et al., Electromagnetic Waves, Chapters 2, 3, 4, and 8, pp. 46-176 and 336-405 (Prentice Hall Upper Saddle River, New Jersey 1998).
Stark III, Joseph C., "Wireless Power Transmission Utilizing a Phased Array of Tesla Coils", Master Thesis, Massachusetts Institute of Technology (2004).
Stewart, W., "The Power to Set you Free", Science, vol. 317:55-56 (Jul. 6, 2007).
Tang, S.C. et al., "Evaluation of the Shielding Effects on Printed-Circuit-Board Transformers Using Ferrite Plates and Copper Sheets", *IEEE Transactions on Power Electronics*, vol. 17:1080-1088 (Nov. 2002).
Tesla, Nikola, "High Frequency Oscillators for Electro-Therapeutic and Other Purposes", *Proceedings of the IEEE*, vol. 87:1282-1292 (Jul. 1999).
Tesla, Nikola, "High Frequency Oscillators for Electro-Therapeutic and Other Purposes", *The Electrical Engineer*, vol. XXVI, No. 50 (Nov. 17, 1898).
Texas Instruments, "HF Antenna Design Notes—Technical Application Report," Literature No. 11-08-26-003, 47 pages (Sep. 2003).
Thomsen et al., "Ultrahigh speed all-optical demultiplexing based on two-photon absorption in a laser diode," Electronics Letters, 34(19):1871-1872 (Sep. 17, 1998).
UPM Rafsec, "Tutorial overview of inductively coupled RFID Systems," 7 pages (May 2003).
Valtchev et al. "Efficient Resonant Inductive Coupling Energy Transfer Using New Magnetic and Design Criteria". IEEE, pp. 1293-1298, 2005.
Vandevoorde et al., "Wireless energy transfer for stand-alone systems: a comparison between low and high power applicability", Sensors and Actuators, vol. 92:305-311 (2001).
Vilkomerson, David et al., "Implantable Doppler System for Self-Monitoring Vascular Grafts", *IEEE Ultrasonics Symposium*, pp. 461-465 (2004).
Villeneuve, Pierre R. et al., "Microcavities in photonic crystals: Mode symmetry, tunability, and coupling efficiency", *Physical Review B*, vol. 54:7837-7842 (Sep. 15, 1996).
Yariv, Amnon et al., "Coupled-resonator optical waveguide: a proposal and analysis", *Optics Letters*, vol. 24(11):711-713 (Jun. 1, 1999).
Yates, David C. et al., "Optimal Transmission Frequency for Ultralow-Power Short-Range Radio Links", IEEE Transactions on Circuits and Systems—1, Regular Papers, vol. 51:1405-1413 (Jul. 2004).
Yoshihiro Konishi, *Microwave Electronic Circuit Technology*, Chapter 4, pp. 145-197 (Marcel Dekker, Inc., New York, NY 1998).
Ziaie, Babak et al., "A Low-Power Miniature Transmitter Using a Low-Loss Silicon Platform for Biotelemetry", *Proceedings—19th International Conference IEEE/EMBS*, pp. 2221-2224, (Oct. 30-Nov. 2, 1997) 4 pages.
Zierhofer, Clemens M. et al., "High-Efficiency Coupling-Insensitive Transcutaneous Power and Data Transmission via an Inductive Link", *IEEE Transactions on Biomedical Engineering*, vol. 37, No. 7, pp. 716-722 (Jul. 1990).

\* cited by examiner

POWER GENERATION FOR IMPLANTABLE DEVICES

This application is a continuation-in-part of U.S. patent application Ser. No. 12/131,910 filed Jun. 2, 2008 which claims priority to U.S. provisional application 60/977,086 filed on Oct. 2, 2007 entitled "Systems and Methods for Wireless Power", 60/941,286 filed on Jun. 1, 2007 entitled "Systems and Methods for Wireless Power", 60/941,287 filed on Jun. 1, 2007 entitled "Power generation for implantable devices", all of which are incorporated herein by reference herein.

The invention relates to providing energy to implantable devices and using wireless energy which has been transmitted and energy derived from natural resources which are available in the patient's environment with an emphasis on utilization of RF energy, heat, light, and motion.

BACKGROUND

Implantable medical devices use electrical power to operate and provide therapies which can include monitoring and stimulation. When therapy is provided or adjusted programmably, using an external patient controller, communication between the external and internal components of the medical system also requires power. An implantable device can monitor the heart and alert the patient when an abnormal cardiac state occurs so that they may seek intervention such as is described in U.S. Pat. No. 6,609,023 and US20070016089, both to Fischell et al. The implantable device may also use this monitoring in delivering responsive therapy such as pacing the heart, delivering a drug, or stimulating nerve tissue of the brain or body as described in U.S. Pat. No. 6,066,163, to John.

An implantable medical device can be a neurostimulation device which performs sensing and/or modulation of neural activity in the treatment of, for example, epilepsy, motor, pain, psychiatric, mood, degenerative, and aged-related disorders. Neurostimulators can be located in the brain, in the skull, or in the body. This last embodiment will require that electrode leads transverse the neck so that they can stimulate their intended neural targets within the brain. Vagal and cranial nerve stimulators may also be used for therapies related to modulation of the brain or body (as may occur directly or by way of an intervening neural target). Implantable medical devices may be placed throughout the body to modulate the activity of different organs and biological processes, and include devices used in the provision of therapy for eating disorders, pain, migraine, and metabolic disorders such as diabetes. As the duration of sensing, processing, monitoring, and stimulation increases the amount of power needed will also increase.

The reliability and longevity of a power source is major issue in operating implantable medical devices. Numerous advances have addressed power requirements including improvements in materials, (re-)charging methods, and technologies. Incorporation of dual battery paradigms has also provided benefits since the two batteries can differ in characteristics of energy storage, chemistry and power output capacities, in order to, for example, reach a compromise between high-energy output and sustainability. Implantable devices themselves have also been improved with features such as "sleep" and "low power" modes, where less energy is needed. Regardless of these improvements, all device operations require power, including monitoring, processing of monitored data, stimulation, and communication with external devices.

A top reason for surgical removal of neurostimulators and other types of implanted devices is longevity of the power source. The need for surgical removal of an entire implanted device traditionally occurs because the battery is integrated into the device itself. This design-related issue can be addressed somewhat by having a separate skull-mounted power module which resides adjacent to the neuronal-stimulator. However, surgery for selective removal/replacement of the power source is still invasive. Further, aside from issues of replacement, in ongoing use of implanted devices, a more robust supply of power can provide improved therapy.

The current invention can incorporate a number of existing technologies such as U.S. Pat. No. 6,108,579, which discloses a battery-monitoring apparatus and method which includes features of tracking power usage, monitoring battery state, and displaying the estimated remaining life of the battery power source. U.S. Pat. No. 6,067,473 discloses a battery-monitoring apparatus and method which includes features of providing audible warnings of low battery life using both tones and pre-recorded verbal warnings of battery depletion. U.S. Pat. Nos. 5,957,956, 5,697,956, 5,522,856, and US 20050021134 to Opie, and 20050033382 to Single, disclose devices having features such as: relatively small mass and a minimal rate of power consumption; means for optimizing current drain; improved shelf storage capacity; minimizing the power requirements of battery power sources; temperature regulation of the power source; and dual battery implementation including use of back-up battery to avoid power disruption. U.S. Pat. No. 7,127,293 to MacDonald describes a biothermal power source for implantable devices and describes methods and materials which are suitable for use in the current invention.

There is a need to provide an improved power supply means for recharging of a power supply of an implantable medical device. Power supply improvements will allow improvements in the performance of the device. Recharging should not require recharging or replacement of the power source in a manner which is unreliable or which places an undue burden on the patient.

The invention provides improved power harvesting, generation and supply and can rely upon naturally occurring sources of energy for at least a portion of its recharging needs. The invention also provides improved power harvesting of transmitted energy.

SUMMARY

A rechargeable power module for powering implantable devices includes a power storage module connected to said implantable device and a power charging module operatively connected to the power storage module.

When the power charging module harnesses thermoelectric power, it has at least a first thermal module and a second thermal module which provide power from a thermal gradient. These two modules can be intra-cranially and extra-cranially disposed, respectively. The power charging module is configured for generating an electrical current from a thermal energy gradient, and for charging said electrical storage module with said electrical current. The rechargeable power module also contains control circuitry for controlling power related operations, as well as charge monitoring circuitry for monitoring rates and levels of charge of the power storage module. The rechargeable power module may also contain alerting circuitry for generating an alert signal whenever the extent to which said electrical storage device is being charged, with said electrical current, falls below a specified value. A disruption module can break the physical connection between the first and second thermal modules, or between the rechargeable power module an components of the implanted device.

When the power charging module is a light-based power charging module, it can have at least one extra-cranially disposed surface that is configured for generating an electrical current from said light source (e.g., the sun or a synthetic means), and for charging said power storage device with said electrical current.

When the power charging module harnesses RF energy which is ambient and naturally occurring, or which is actively transmitted by a transmitter device, then an antenna has at least one extra-cranially disposed surface which is disposed for harnessing the RF energy. The energy harvesting antenna may also be used for transmission of data, and can be disposed within a ferrule that resides within the skull, within the top side of a neurostimulator device disposed within the ferrule, or within the ferrule itself. When the implanted device is a neurological or cardiac device having leads, then one or more of these leads, as well as sheaths which house the leads can be used, at least a portion of the time, as an antenna for energy or data transmission or reception.

The power charging module may utilize external devices which alter temperature, light levels, magnetic or RF energy available for recharging the power module.

The rechargeable power supply can also contain an alerting module for providing energy-related alerts to a user and a historical charge module which can be configured to generate an alert signal related to power consumption and harvesting. For example, an alert may be sent whenever the cumulative extent to which said electrical storage device is being charged with said electrical current falls below a specified value.

In accordance with some implementations, a wirelessly powered medical system includes: a wireless power transmitter; and an implantable medical device including: a wireless energy harvesting module configured for harvesting at least one type of wireless power; a power management module configured for managing, monitoring, and storing harvested power harvested by the energy harvesting module; a control module configured for controlling the power management module and for creating and storing in a memory module a historical power record, said record comprising at least one of amount of harvested wireless power and amount of power consumed as a function of time; and a communication module configured for providing communication between the implantable medical device and at least one external device. The at least one external device can be an external patient controller configured to provide communication between the implantable medical device and the wireless power transmitter and to display at least one historical value related to at least one of power harvesting and power consumption, the value being based upon data from the historical power record that is communicated to the external patient controller from the implanted device.

In some implementations, the external device is an external patient controller that is configured to display at least one historical value reflecting harvested energy as well as an indicator of a target amount of energy which should have been harvested. The target amount of energy which should have been harvested can be defined as a function of time. The target amount of energy to be harvested can be a value that is programmably defined and adjustable. The target amount of energy to be harvested can be a value that is calculated upon data sensed by a sensor located in the external device. The target amount of energy to be harvested can be a value that is calculated upon data sensed by a sensor located in the external device using a transfer function to estimate the amount of energy that should have actually been received by the harvesting module of the implanted device.

There are further provided methods for increasing wireless energy recharging capabilities of the system including methods for increasing the thermal gradient used to generate power and increasing the wireless energy harvesting by increasing the wireless energy which is available, received, and harvested by the implantable power harvesting device.

BRIEF DESCRIPTION OF THE DRAWINGS

Features of the invention will be described by reference to the specification and to the following drawings, in which like numerals refer to like elements, and in which.

The present invention will be described in connection with a preferred embodiment. There is no intent to limit the invention to the embodiments described. The intent is to generalize the principles disclosed here to all alternatives, modifications, and equivalents as may be included within the spirit and scope of the invention as disclosed within the following specification and claims.

DETAILED DESCRIPTION

Figure 1:
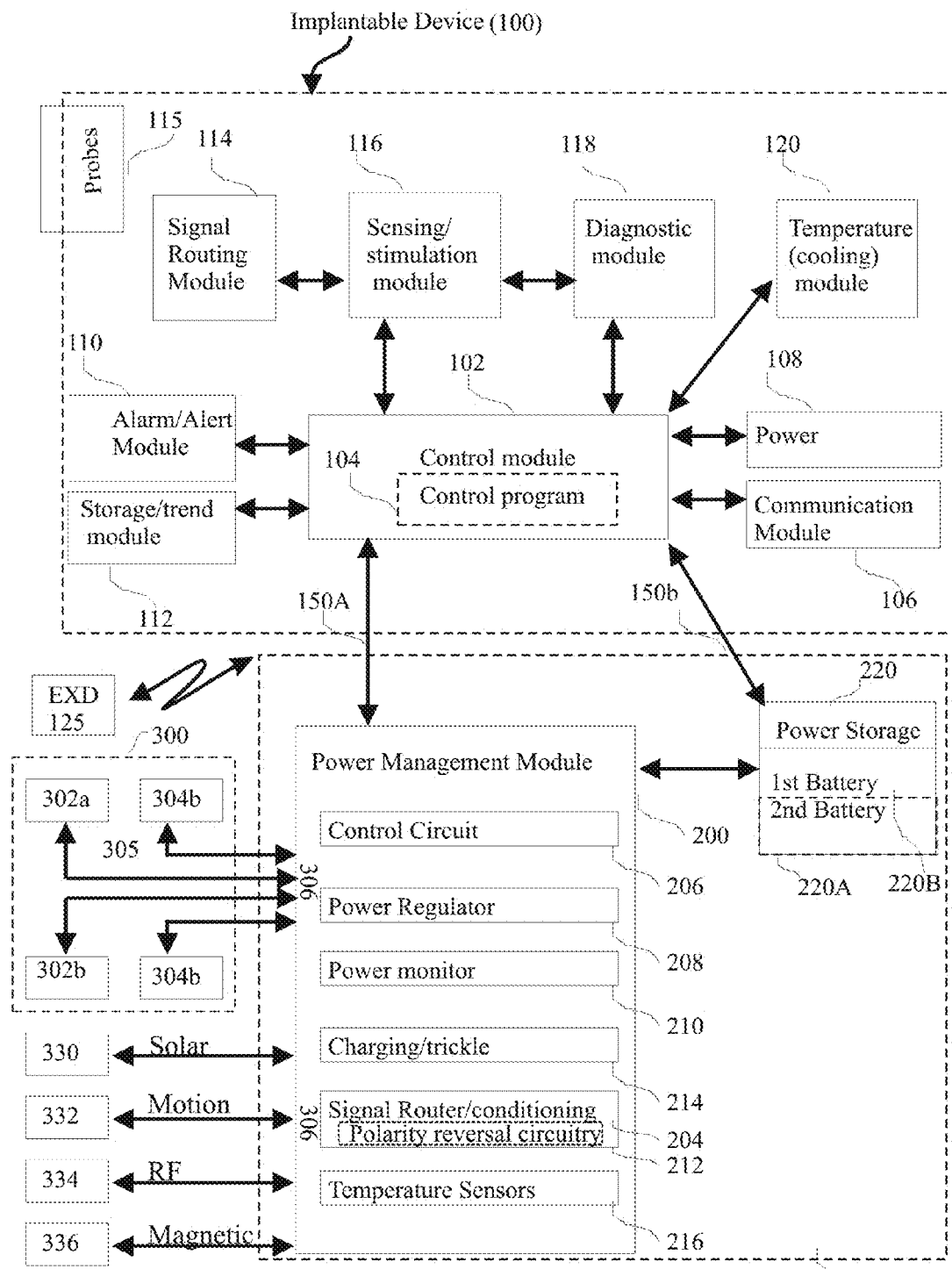
FIG. 1 shows a schematic diagram of one preferred implantable device for operating using a rechargeable power system of this invention.

FIG. 1 is a block diagram of an implantable medical device 100 and rechargeable power system 10 which in a preferred embodiment functions as a multi-modality charging system, but which may be restricted to a single type of energy harvesting. The implantable device 100 may be similar to many conventional generic implementations of neural or cardiac assistive devices, such as having a control module 102 which implements a therapy as defined in at least one control program 104. The control module 102 controls and communicates with all the other modules of the device 100 in order to provide therapy as intended. Accordingly, under control of the control module 102, the signal sensing and stimulation module 116 provides sensing of data, and stimulation, respectively, from probes 115 operatively positioned within the tissue of the patient (e.g. electrical, chemical, sonic, or optical probes) or within the device 100 itself (e.g., acceleration, level/tilt sensors, or thermal probes). Sensed data can be analyzed by the diagnostic module 118 which can detect and/or quantify medically relevant events. In response to the detection of medically relevant events, the control module may responsively provide stimulation to a patient 6 or can issue an alert signal such as a sonic signal or a vibration using a probe 115 which is a motor. Alternatively, the device 100 may send an alert signal using a communication module 106 which can provide communication between the implanted device 100 and an external patient device 125 such as a patient programmer device which is implemented in the form of a pager-like device, with a display screen, LEDs, acoustic transducers, and buttons for patient input operations. In addition to memory storage such as RAM and EEPROM, the device 100 can have a storage/trend module 112 which may contain a queriable database, and where information such as parameter values, and historical records related to device operation and treatment may be stored. Temperature regulation (Heating or cooling) both of components within the device 100 or external probes 115 can occur under the control of the temperature module 120. In one preferential embodiment a temperature probe 115 is provided which allows cooling of the brain to occur by using a peltier-based probe configured with an extra-cranial heat sink and intracranial cooling surface. A power module 108 may also be provided in order to provide operations related to power management and monitoring, and for storing protocols and parameter values which enable the control module 102 to communicate and control the rechargeable power system 10. Control conduits 150a and 150b are comprised of at least one metallic or optical pathway which provides power and/or control signals to be communicated between the device 100 and the rechargeable power system 10.

The rechargeable power system 10 can harness power using at least one of thermoelectric derived energy 300, solar derived energy 330, motion-based energy 332, RF harnessed energy 334 using far-field and medium-field techniques, and energy harnessed from magnetic fields using near-field techniques 336. When utilizing far-field techniques the modules 334 can be based upon Powercast technology which provides for energy harvesting of both ambient and transmitted energy, and may include at least one antenna and associated harvesting circuitry. Some related technologies for transmission and reception, which can be utilized by the current invention have been filed by Powercast and include patent applications for example, US20070010295, US20060281435, US20060270440, US20060199620, US20060164866, and US20050104453. Some related technologies filed by eCoupled include, for example, Inductive Coil Assembly (U.S. Pat. No. 6,975,198; U.S. Pat. No. 7,116,200; US 2004/0232845); Inductively Powered Apparatus (U.S. Pat. No. 7,118,240 B2; U.S. Pat. Nos. 7,126,450; 7,132,918; US 2003/0214255); Adaptive Inductive Power Supply with Communication (US 2004/0130915); Adaptive Inductive Power Supply (US 2004/0130916); Adapter (US 2004/0150934); Inductively Powered Apparatus (US 2005/0127850; US 2005/0127849; US 2005/0122059; US 2005/0122058. Splashpower has obtained patents such as U.S. Pat. No. 7,042,196. All these patents and patent applications are incorporated by reference herein and describe technologies which will be generally understood herein as wireless power systems that relate to the invention including RF- and near-field-induction-related wireless power transmission and wireless power reception.

The energy harnessing modules 300, 330-336 are connected via the signal router 204 of the power management module 200 to control circuit 206 by leads 306 which provide electrical contact between the harnessing modules 300, 300-336 and the power management module 200. Control circuit 206, in turn, is operatively connected to power regulator 208 circuitry which includes safety and isolation components. The power regulator 208 provides direct current to at least one battery of a first battery 222a, and a second battery 222b of the energy storage module 220. Although only 2 batteries are shown here, many batteries, capacitors, may be used in the power storage module, and these may be stored together, or in physically distinct regions of the device, and even outside of the device. Although the electrical storage module 220 would normally contain at least one battery 222a,b which can be rechargeable, other electrical storage devices can be used such as traditional capacitors or capacitors constructed of carbon, nanomaterials, or other suitable materials. The capacitors can be comprised of multilayer dielectric materials having capacitors and insulators or other type of hybrid compositions (e.g., U.S. Pat. No. 6,252,762 "Rechargeable hybrid battery/supercapacitor system"; U.S. Pat. No. 5,993,996 "Carbon supercapacitor electrode materials"; U.S. Pat. No. 6,631,072 ("Charge storage device"); and U.S. Pat. No. 5,742,471 ("Nanostructure multilayer dielectric materials for capacitors and insulators"). The storage module 220 may be designed without a battery, as may occur, for example, if the power module 108 of the implanted device 100 is to be primarily relied upon or if the device will rely upon external energy sources during its operation.

A power monitor 210 is connected to the storage module 220 and contains sensors for monitoring the power level of batteries 220a,b as well as rates of charge and discharge. The power monitor 210 can cause the power management module 200 to issue an alert signal using the alert module 110 of the implantable device 100 and is capable of providing a warning to a user when the power being generated, stored, or which is in reserve is inadequate. The probes 115 can be used to generate audible, visual, vibrator, or other type of alerts to provide warnings of low battery life. An external patent programmer 125 can display a history of usage, recharging related historical information, and information related to the remaining life of the battery, for example, as may be similar to that shown in FIG. 5.

In a number of preferred embodiments the rechargeable power system 10 relies upon the Seebeck effect which is also known as the "Peltier-Seebeck effect" or the "thermoelectric effect". The Seebeck effect is the direct conversion of thermal differentials to electrical voltage. It is often produced using two junctions of dissimilar temperatures and metals. U.S. Pat. No. 5,565,763 (Thermoelectric method and apparatus') and U.S. Pat. No. 4,095,998 (Thermoelectric voltage generator') describe implementing the Seebeck effect within energy producing devices.

FIG. 1, shows thermoelectric module 300 that has at least a first thermal module 302 and a second thermal module 304, which are connected to the power management module 200 using leads 306. The electrical leads 306 can be routed by a signal router 204 through a polarity reverser 212 prior transmission of these signals to the control circuit module 206. The polarity reverser 212 is used to adjust for the case in which the temperature of a first thermal module 302 is higher than the temperature of a second thermal module 304, and also when the opposite is true. This adjustment is necessary since the polarity of the electric current produced the two situations will be reversed. If the polarity reversal circuitry 212, did not exist then the electrical current produced by the thermoelectric module 300 would not be utilized by power management module 200 in one of either the first or second situation. Various polarity circuit implementations are well known (e.g. see review in U.S. Pat. No. 7,127,293, "Biothermal power source for implantable devices").

Although the device 100 of FIG. 1 may operate alone, when the device is implemented as part of a network of implanted devices, power may be generated, stored, and supplied in a distributed fashion using components which are either within the device 100 housing or distributed. A device which is similar to the BION stimulation device, produced by Advanced Bionics may serve as the device 100. When the device is implemented as a BION, at least one probe 115 can serve to provide sensing or stimulation operations and the housing may serve as a reference or ground source or as part of a bipolar probe. A portion of the BION device can serve as at least one antenna related to wireless power and data transmission. In a device with such small mass and volume, it may be increasingly important to temporally separate charging and non-charging related operations as can occur under control of the control module 102 working in conjunction with the power management module 200. Alternatively, the wireless power transmission device can be synchronized with the BION's operations so that power transmission occurs only during intervals when the BION is not engaged in particular non-charging treatment operations. When a network of BIONs are charged by at least one wireless energy harvesting device, which may be incorporated into a rechargeable power supply, then either a master BION may control operations and allocations of wireless power, or any of the BIONS can communicate requests for or adjust operations related to power harvesting.

Figure 2A:
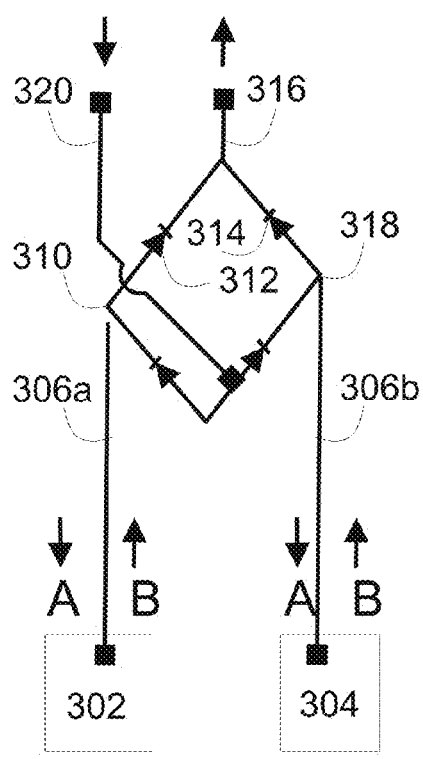
FIGS. 2A-2C shows three types of polarity reversing devices that may be used to harness power such as thermoelectric power by the system of FIG. 1.

FIG. 2A is a schematic diagram of a polarity reversal device 310a that can be used to address opposite temperature differentials that result in forward and reverse currents (which can be implemented within the polarity reversal module 212 of FIG. 1). When lead 306a is negative, electrons flow to point 310, through diode 312, and then through path 316. If the polarity is reversed due to a reversal of the relative temperatures of thermal module 302 and 304, electrons will flow through path 306b, through to point 318, through diode 314, and then through path 316. In either case, the temperature difference between the two thermal modules 302,304 will cause power generation. This feature is necessary with biological thermal energy generation since the temperatures surrounding the thermal modules may unpredictably fluctuate both in terms of absolute levels and also relative to each other. This circuit has previously been described in the '293 application.

Figure 2B:
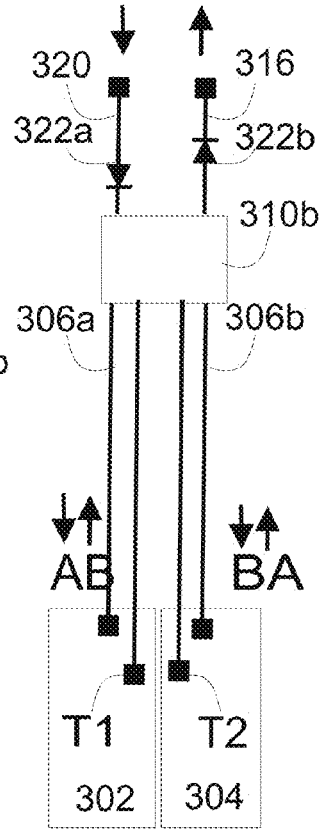

FIG. 2B shows that the polarity reversal device 310b can also be implemented in the form of a router which is guided by a temperature signal from sensors T1, T2 which are placed in the thermal modules and which communicate with temperature sensor module 216, which routes electrical signals of paths 306a and 306b, to 320 and 316, respectively (or 320 and 316, respectively), depending upon whether T1>T2 or T2>T1. Diodes 322a and 322b ensure that current flows in the correct directions.

Figure 2C:
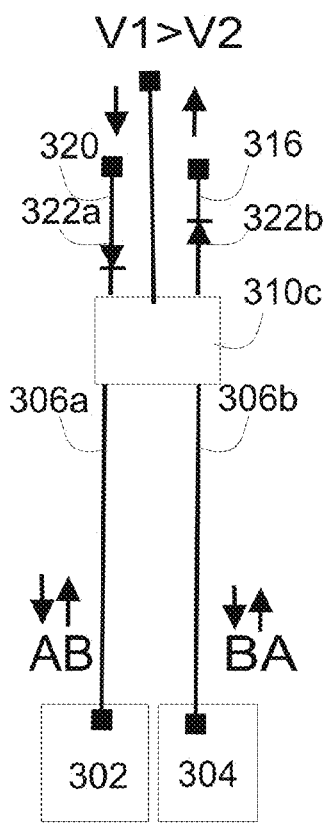

FIG. 2C shows that the polarity reversal device 310c can also be guided by a voltage circuit that can be located in the control circuit module 206 and that tests the voltage produced by connecting paths 306a and 306b to different output paths 320 and 316 and determining which combination results in the maximum desired voltage and polarity. Again diodes 322a and 322b ensure that current flows in the correct directions.

Figure 3:
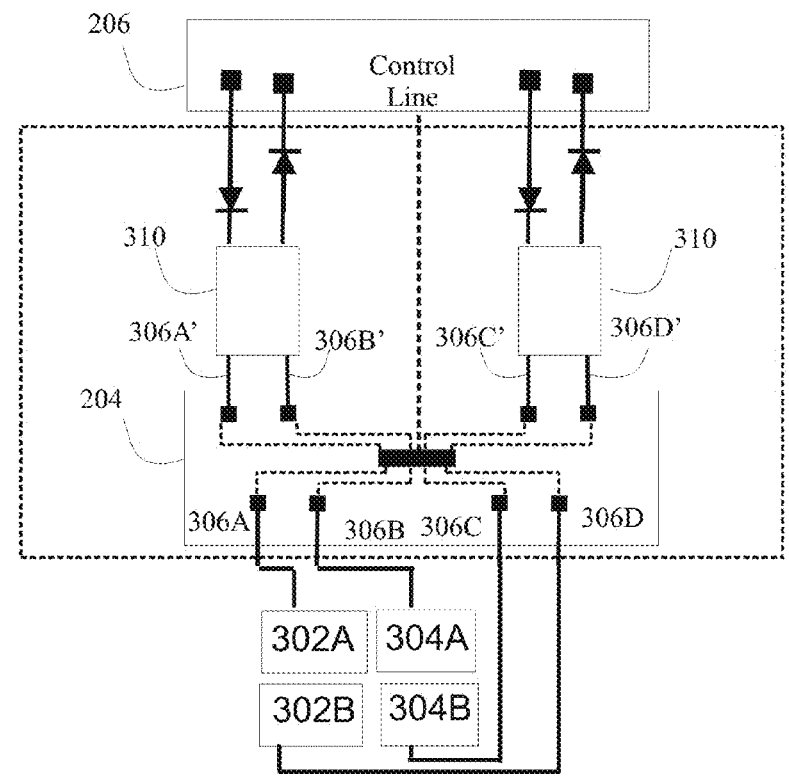
FIG. 3 shows a diagrammatic representation of a power harvesting module which improves power harvesting related to thermal-based power generation.
Figure 4A:
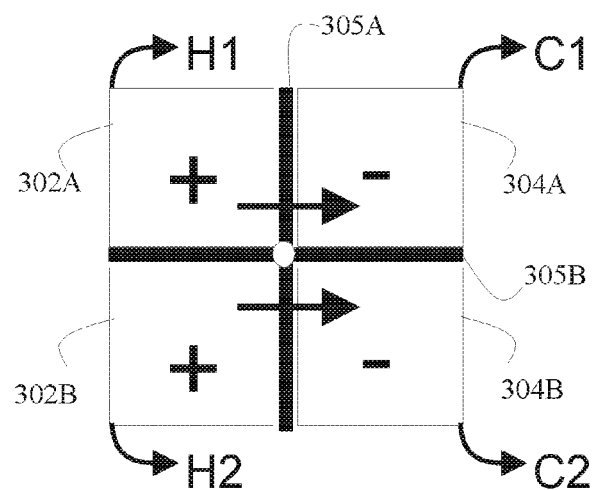
FIGS. 4A-4C shows three types of thermal gradients which are applied to thermal modules, and which lead to improved energy harvesting using the routing device of the system of FIG. 3.
Figure 4B:
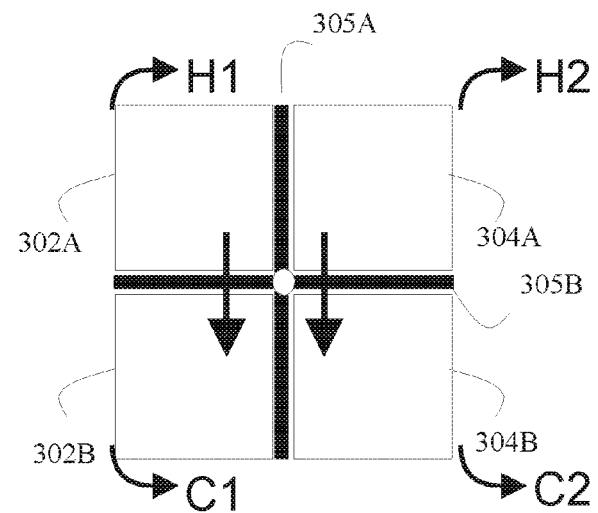

FIG. 3 shows a signal router module 204 which is used to obtain current in a number of different situations which may arise. The router module 204 is connected by leads 306 to thermal modules 302A,B, and 304A,B. Normally thermal modules 302A and 304A serve as a first thermal module and a second thermal module and thereby form a first thermal pair 303A (which is formed conceptually and is not shown). The thermal pair may be positioned in the patient so that 302A is normally more likely to be warmer than 304A. Likewise thermal modules 302B and 304B form a second thermal pair 303B (which is formed conceptually and is not shown). In one embodiment a PNP layer 305A occurs between the first thermal module 303A pair, while another PNP layer 305B occurs between second pair of thermal modules 303B (as shown in FIGS. 4A-4B). The Table 1 shows three exemplary conditions:

TABLE 1

| Thermal Probe | Condition 1 | Condition 2 | Condition 3 |
| --- | --- | --- | --- |
| 302A | 38 | 35 | 36 |
| 304A | 35 | 38 | 35 |
| 302B | 39 | 36 | 38 |
| 304B | 36 | 39 | 39 |

Condition 1 shows the four thermal modules with relative temperatures that may occur in "normal" operation. Condition 2 shows temperatures that may occur in an "opposite" operation, where the polarity reversal devices of FIG. 2A-C may be used. Condition 3 shows temperatures which differ by only 1 degree and for which the second thermal pair would require a polarity inverter. In this last instance, using the signal router 204 of FIG. 3, the thermal modules can be re-assigned to form new thermal pairs, notably 302A can be paired with 302B to obtain a difference of 2 degrees (rather than 1), and 304A can be paired with 304B to obtain 4 degrees (rather than 1).

In one embodiment, the voltage produced by thermal pair 1 is combined with the voltage produced by thermal pair 2, by circuitry in the power manager 200. In another embodiment, the thermal modules within thermal pairs 1 and 2 are electronically fused so that 304A and 304B form the "cold" thermal pair (paths 306A and 306C are routed to 306c') and 302A and 302B form the "hot" thermal pair (paths 306B and 306D are routed to 306D'). In this case and the voltage produced is a function of the average differential between these two new functional modules. Combining the output voltages from the two thermal pairs should likely be equivalent to what is obtained by rearranging the electrical paths to form 1 new "combination" thermal pair, but due to real world differences one of these embodiments may perform slightly better than the other. Further, any performance differences between these two strategies can be a function of the ranges of temperature differential, and the power management module 200 can select which strategy is used based upon selected ranges as well as other operational factors (e.g. increased temperature variability in one of the thermal modules).

The power management module 200 can be powered off of the energy harvesting modules 300, 330-336 or by the batteries 220. It is expected that when the temperature differential is greater than 2 degrees Celsius, electrical energy will be produced sufficiently to run the control circuit 206. When the temperature differential is closer to 1 degree Celsius, adequate temperature differential may still be sufficient to provide adequate electron flow to control circuit 206.

Figure 4C:
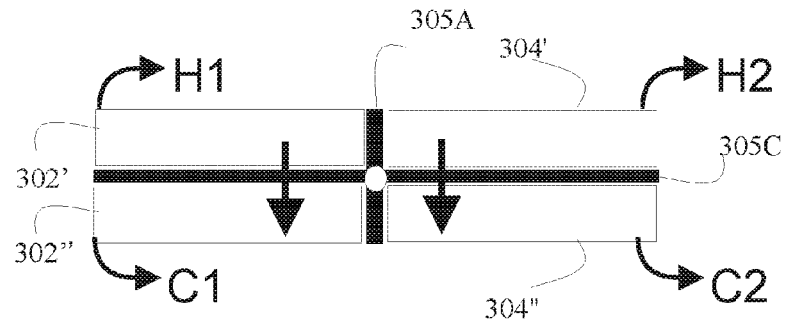

FIGS. 4A, 4B, and 4C show a thermal module having 8 thermal plates which can be configured to form a plurality of thermal pairs depending upon the existing temperature differentials. Different thermal pairs are functionally created by rearranging electrical paths 306 so that the different modules are functionally paired (form positive and negative generating components of a circuit). FIG. 4A shows how charge would flow from the left to the right of the thermal module 300' when the plates on the left side of the thermal module are hotter than the plates on the right. When the thermal gradient is reversed, the polarity reversal circuits 310a-310c of FIG. 2A-FIG. 2C can be used. FIG. 4B shows a redistribution of the thermal pairs as a function of the thermal gradient being oriented 90 degrees from that seen in FIG. 4A. In this case, if the same charge pairs were used then there would not be much thermoelectric output. However, by redefining the thermal modules the functional thermal gradient is increased. The thermal pairs created by 302A and 304A, and 302B and 304B, are redefined as 302A and 302B and 304A and 304B, in order to achieve this novel feature of the invention, wherein electrons travel through PN stack sections which are oriented at 90 degrees to each other. In FIG. 4C, the thermal gradient runs from the top of the thermal module to the bottom, and again, the thermal modules are reorganized so that thermal pairs are created between the top 302' and bottom 302" plates on the left, and right (304' and 304", respectively) side of the thermoelectric module (again an angle of 90 degrees is used to establish a new orientation, but along a different axis of rotation).

Although a square configuration is shown, it is understood that the modules may be of various shapes and sizes, and may be adjusted according to the sites of implantation. Materials may also permit the modules to be constructed so that these have some degree of flexibility. While a single structure is shown in each of the FIGS. 4A-4C, the structures may be imparted within a larger grid structure which may also be square or not. Although illustrated with respect to thermal gradients, and resulting electrical outputs, the same logic would be used in order to utilize the thermoelectric modules as Peltier-based cooling devices, wherein applying currents to the different pairs would produce different patterns of heating and cooling. Further, rather than being restricted to thermoelectric generation, other modalities such as light, sound (including ultrasound), motion (i.e. kinetic), and RF harvesting can be used with the systems and methods used by devices shown in FIG. 1 trough FIG. 5 which depend upon displacement of electrical charge in the generation and storage of power.

The PN stacks 305 are here shown as thin layers sandwiched between thermoelectric pairs. The PN stacks can be comprised of several PN layers which are oriented and organized in a number of fashions as is well known. U.S. Pat. No. 6,207,887 (Miniature milliwatt electric power generator') shows FIGS. 12a and 12B indicating that use of smaller PN elements within the PN stacks produces higher output as a function of thermal gradients, and accordingly the PN stacks utilized by the invention may rely upon smaller elements.

Power Management, Reporting, and Control.

Figure 5:
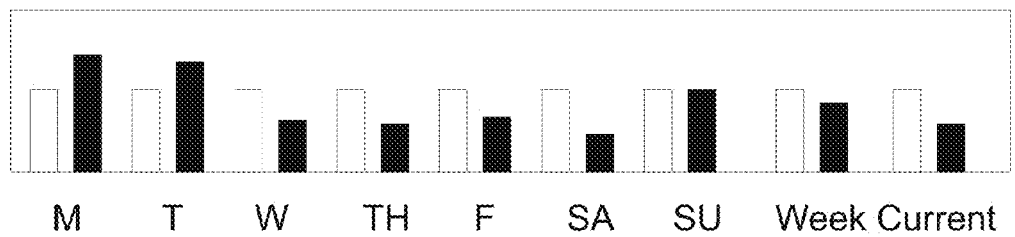
FIG. 5 shows an upper plot summarizing energy harvesting levels across a 1 week interval, as well as average and current energy levels and shows a lower plot which can represent the energy harvested over the last 24 hours, the energy harvested as function of time of day averaged over the last week or month, and related plots such as target energy harvesting levels as a function of time.
Figure 5:
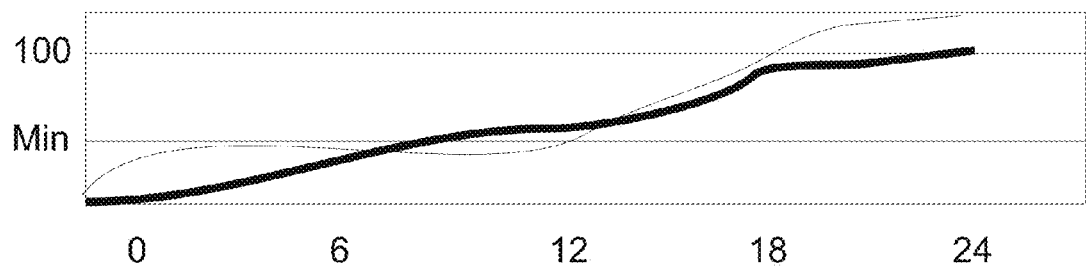

The power monitor 210 may use the memory 112 of the device 110 to create a historical record of power generation and consumption such as is graphically shown in FIG. 5. FIG. 5 shows two exemplary plots of the data that may be stored in module 112, as these may be displayed on the external patient programmer 125. The upper panel is a plot of a graph which shows a daily amount of wireless energy that was harvested over the last 7-day period. The white bars represent the daily target which the patient is expected to meet, and these may be set, programmably defined, or defined/adjusted, for example, as a function of time, power usage, power generation, treatment needs, or user input. Additionally, in one embodiment, the graph shows the cumulative amounts of power created/harvested over the entire week (with a change in units of energy) and the current amounts of power in the power storage device. The black bars indicate actual energy created/harvested. By providing data about historical energy which was created/harvested or used, the patient 6 can gain understand about how daily activities alter power harvesting and usage. The power monitor 210 can also be configured to send alerts when energy harvesting increases above a specified level or drops below a specified level, and a duration criterion can also be used, in order to assist patients in monitoring their energy usage.

In the lower panel of FIG. 5 a graph shows the cumulative power generated/harvested in the last 24 hour period (thin line) as well as the anticipated power which should have been created (thick line). Anticipated or "target" power levels can, for example, have been previously determined by a physician, or can have been computed based upon historical activity of the patient. In this case, the graph shows that from midnight until 6 a.m. the power created was more than the target amount, while from 6 to around noon, the power created was less. By the end of the day the patient has generated/harvested a surplus amount of power compared to the target amount (100%), and has well surpassed the target power generation level, which may be a minimum threshold limit value.

In order to keep the battery 220 from becoming discharged below a particular level the alert module 110 can issue alerts when power levels become critically low so that the patient will make certain that the battery 220 is recharged in the near future. The alert module 110 may also be configured to shut down the device 10, or portions of the device 10, or to limit operation to certain functions defined as a lower power state, when a particular critical level is reached so that there is enough energy to perform essential operations, such as operations relating to recharging the battery.

The re-chargeable power module 10 can be configured so that if the batteries 220 become completely discharged, the module 10 can supply emergency power to the device 100, or can initiate recharging operations using purely wireless power harvesting, if sufficient wireless power becomes available. This type of restart operation can also comprise marking the occurrence of a complete system shutdown in the storage module 112. When a minimum battery power is reached the storage module may store the time of the shut-down in memory of module 112. Accordingly, upon restart, the current time and date can be re-established using an external patient device 125, in order to calculate how long the device was non-functional. Storing power 'shut-downs' and 'restarts' in the historical module 112, may also lead to the generation of an alert signal being sent by the alarm module 110, to a central station which the device communicates with using the communication module 106. This is important since if patients are non-compliant with respect to ensuring sufficient energy harvesting, then the implanted device will not provide much therapeutic benefit. Unlike implantable devices which use very little power, when implantable devices are configured to use more energy, it is important that the patient is compliant in ensuring that energy harvesting is sufficient for proper system operation.

In one instance, if the patient had not generated more power than indicated by the "minimum power generation threshold level" by a selected time (e.g. 6 p.m.) then the alert module would have issued an alert signal to the patient. Rather than displaying results for the last 24 hours, the graph could have been computed upon charging patterns calculated for other prior periods such as the last week or month. In this manner the patient can learn about, for example, how daily activity influences temperature around the thermal modules and can increase their subsequent ability to charge the implanted device as needed. In addition to power generation, other data can be displayed including power usage, temperature of thermal modules, and differential temperatures of thermal pairs (as well as the pairs that were created).

Alert signals can be generated in order to warn the patient when battery power becomes lower than a specified amount, when the average rate of power consumption is more than the rate of power generation for a selected interval, when the slope of residual power by time has a value that is more than a selected level for a specified amount of time, as well as numerous other characteristics related to charging, discharging, and residual power supply. Alerts can also be generated if the temperature as recorded from thermal sensors 115 near thermal modules 300 indicate that temperatures are outside of a normal range for an extended amount of time, for example, in a manner that is not beneficial to generating power in an expected fashion.

Power management and control provided by the power management module 200 is needed for disentangling power related operations from other operations of the device 100. It is likely that in devices 100 which utilize sensing, certain sensing operations should be halted, delayed, attenuated, or otherwise modified during a portion of the charging operations, and subsets of steps related to carrying out these operations, especially if the wireless harvesting includes near-field induction transmitters. In devices 100 which utilize stimulation, certain stimulation operations should be halted, delayed, attenuated, or otherwise modified during a portion of the charging operations, and subsets of steps related to carrying out these operations, especially if the wireless harvesting includes receiving energy which is above a specified level. In devices 100 which utilize communication with external devices, certain communication operations should be halted, delayed, attenuated, or otherwise modified during a portion of the charging operations, and subsets of steps related to carrying out these operations, especially if the data communications include alerting and/or transfer of diagnostic data related to an alert signal. In devices 100 which utilize sensing, stimulation, or communication, transmission of wireless power or power harvesting operations should be halted, delayed, attenuated, or otherwise modified during a portion of the non-recharging operations, and subsets of steps related to carrying out these operations.

Additionally, the re-charging circuitry may be configured to work with the sensing, stimulating, and communication circuitry so that various charging operations and related phenomena which are influencing the sensing, stimulation, or communication subsystems of an implanted device are ignored, compensated for, or otherwise addressed by these subsystems, and associated operations and algorithms. This type of compensation may occur, for example, using communication between the power management module 200 and the sensing/stimulation 116, communication 106, or diagnostic 118 module. Selected non-charging operations can occur simultaneously with charging operations when filters and circuitry are provided to isolate the effects of charging-related operations and treatment related operations. For example electrical artifacts due to charging can be filtered out, subtracted, or made to occur in a time locked manner so that the artifacts occur in a controlled rather than spurious manner.

Thermal Issues of Energy Harvesting, Usage, Storage, and Stimulation.

Figure 6A:
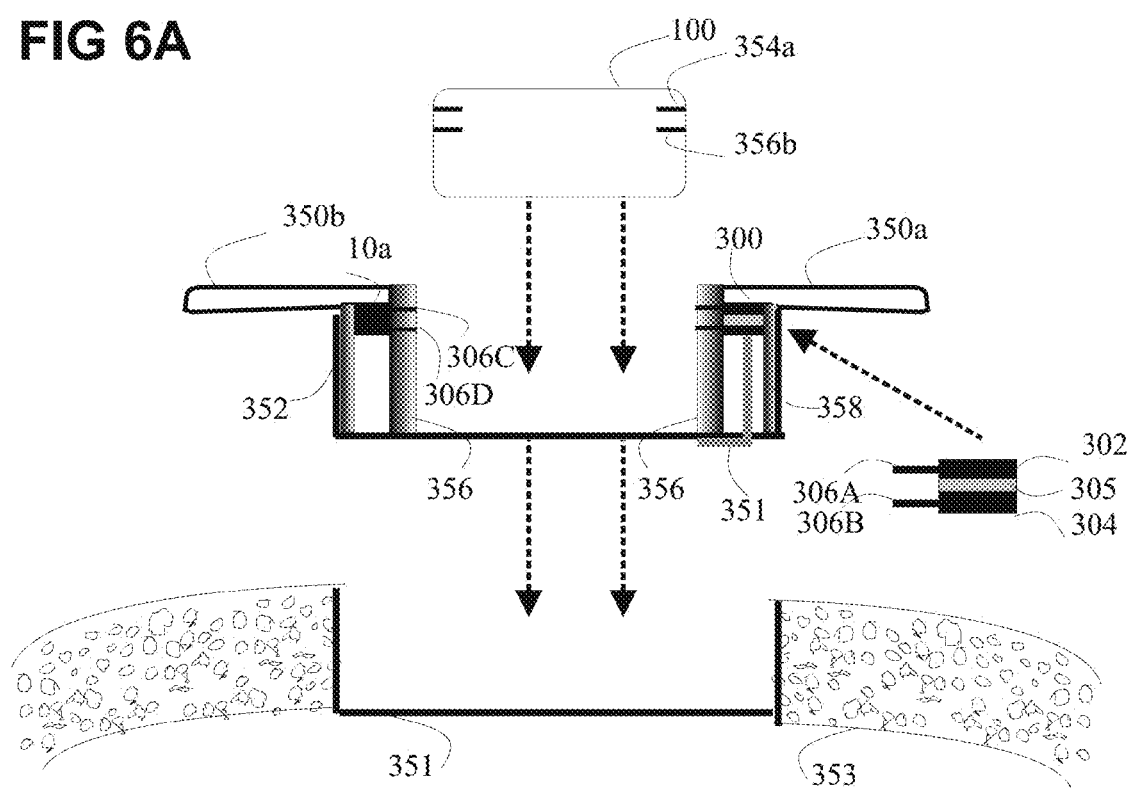
FIG. 6A-6B show schematic representations of skull mounted neurostimulator devices configured for generating power from a thermal gradient and for efficient thermal regulation of brain tissue; and, FIG. 7 shows diagrammatic representation of an extra-cranially disposed energy harvesting device which can be used for increasing the power that is generated using methods generally known as well as those specific to the present invention.
Figure 6B:
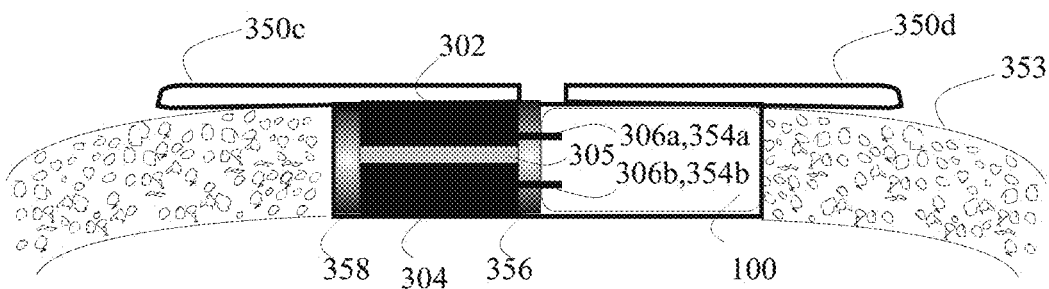
Figure 7:
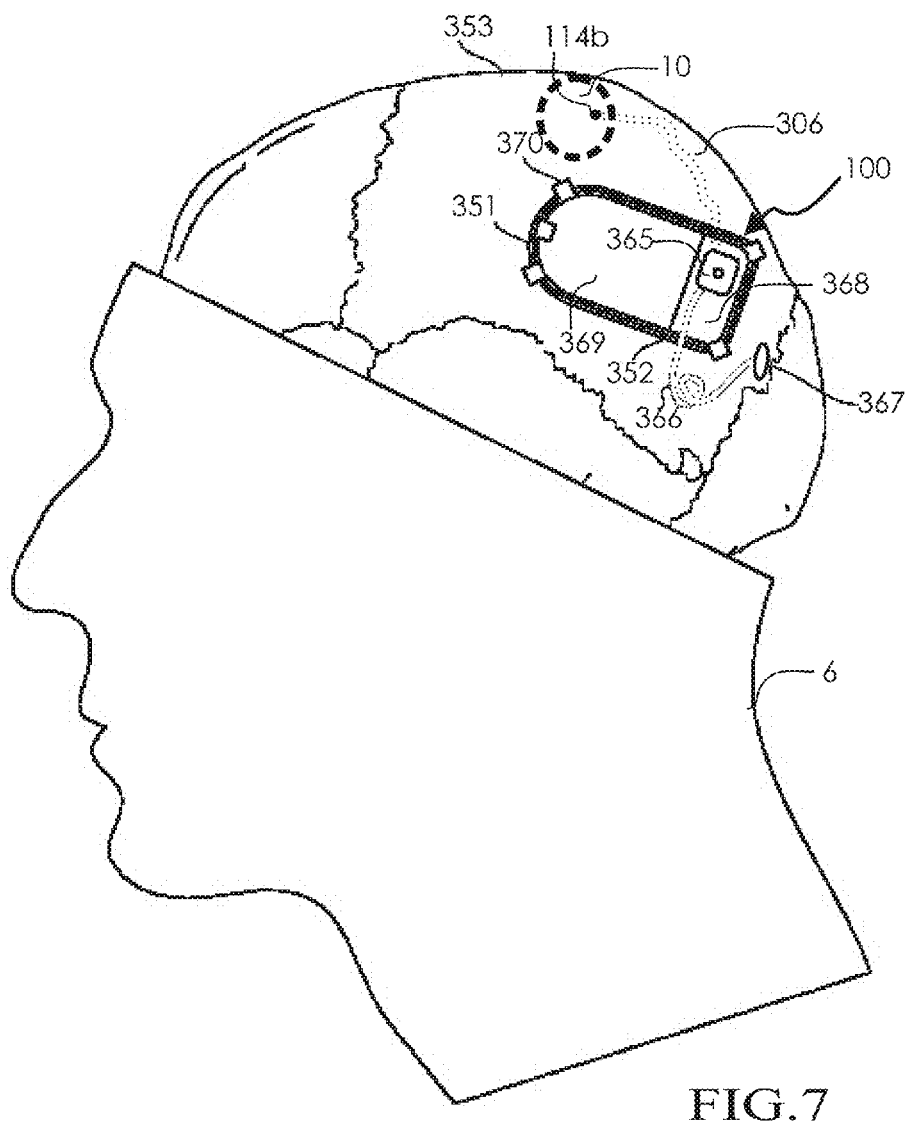

Some preferred embodiments of implanted medical systems which include neurostimulators, ferrules, rechargeable power supplies, and thermal-cooling are shown in FIGS. 6A, 6B, and 7. In FIG. 6A an extra-cranial receiver plate 350a which approximately conforms to the skull may be used to disperse heat away from a skull mounted implantable device 100, which in this instance is a neurostimulator device which resides within a ferrule 352. A thermal module 300 having a thermal pair 302,304 which are separated by a PNP layer 305 supplies power to the device 100 using electrical conduits 306A, and 306B, which will supply voltage in one direction, or the other, depending upon whether one side 302 of the thermoelectric module 300 (which receives or dissipates energy via the extra-cranial receiver plate 350a) is hotter or cooler than the other side 304 (which receives or dissipates energy via the intracranial-cranial receiver plate 351). The power is communicated to the device 100 by electrical contacts 354a, 354b which, respectively, are in contact with electrical conduits 306A, and 306B, which travel through an inner thermal and electrical insulation layer 356. An inner thermal and electrical insulation layer 356, and an outer insulation layer 358, as well as additional insulation layers can be implemented within the device to insulate various components against unwanted thermal and electrical coupling. In one embodiment, the device 100 is normally recharged using solar or thermal means, but when these are insufficient the patients are alerted 110 so that they can charge the device using an external means. In the case of thermal plates 302, 304, the patient can apply a heating or cooling device directly to their skull. In the case of a photovoltaic (i.e. 'solar') energy harvester, patients can go outside into the sun or can apply a light (laser) to their skull.

In FIG. 6A, an extra-cranial receiver plate 350b which approximately conforms to the skull may be used to harness energy using a number of wireless modalities (e.g., light, temperature, sound, RF, induction). It may be configured not only with thermal plates 302/304 and a PN stack 305, but also with solar components 330, motion-based electrical generation components 332 (including sound/vibration harnessing modules), RF components 334, and/or magnetic induction components 336. The receiver plate 350b may comprise one or more skull mounted induction coils, skull-mounted RF antennas, photovoltaic cells, and the like. Utilization of an extra-cranial receiver plate 350b, provides energy harvesting which is more efficient than systems which require that radiant energy travel an increased amount of distance, and through both skull and tissue, in order to reach receivers located intra-cranially. In one embodiment, the device 100 is normally recharged using solar or thermal means, but when these are insufficient the patients are alerted 110 so that they can charge the device using an external means. In the case of an RF or magnetic induction receiver, the patients can act so that the wireless energy transmitter is turned on or brought into sufficient proximity to the receiver 334, 336. The use of skull mounted receiver plates 350a is advantageous because these can be larger than that which might exist when positioned in other parts of the brain or body. Accordingly receiver plate 350b as well as a rechargeable power supply 10a capable of energy harnessing, conversion, and storage of energy can be located distal from the ferrule 352 or device 100, and can send energy to the device 100 via electrical conduits 306C, 306D. For example, a skull mounted photovoltaic device that retained within a distally located receiver plate 350c (similar to that seen in FIG. 7), which resides upon a patient's frontal skull portion (i.e. 'forehead') is well positioned to receive light and may reside across a 1 inch by 1-2 inches area without causing the patient discomfort. The ferrule 352 is configured for residing in a surgically prepared area 351 of the patient's skull 353.

In the case where the receiver plate 350b serves as an induction harvester, it may be divided into at least a first portion and a second portion, each of which may be electrically and thermally insulated from each other, which may make functional (data or power) communication with external devices (and appropriate polarities) and which may further make respective electrical connection with skull mounted components, or a ferrule which communicates with the device, or at least one implanted device itself.

Energy harvesting circuits and antennas can be configured to receive RF energy, or wireless energy which has positive and negative charge polarities. When these components are encased within a metal such as titanium (i.e. when these are within the housing of an implanted device), this encasement may be designed with partitioning, non-conductive, and insulating materials which are disposed within the housing material so as to permit differential charges to be induced on the energy harvesting circuits and antenna's (i.e. in order to circumvent or attenuate field dispersion and isopotential surfaces). Alternatively, the receivers may be independently housed and connected to the implanted device in a manner which enables electrical isolation so that shorting, grounding, and isopotential gradients do not hinder wireless charging functionality.

FIG. 6B shows an embodiment of the invention in which a thermoelectric module 300 and device 100 are disposed in an adjacent horizontal configuration. Energy can be created when the thermoelectric module experiences a temperature differential between the a first element 304 which is on the ventral side and which obtains heat from intracranial sources, and a second element 302, which is disposed dorsally and which can further distribute heat along the energy reception plate 350C. Charge crossing the PN stack 305 causes current to flow through conductive conduits 306A, 306B an into the device 100 through electrical contacts 354a,354b. The PN stack 305 can consist of a multiplicity of n-doped/p-doped thermocouple pairs preferably electrically arranged in series and sandwiched between ceramic plates, although any configuring is possible (e.g., U.S. Pat. No. 6,207,887, but which use different separator elements between the P-type and the N-type elements. Thus, one may utilize epoxy-impregnated paper isolators; see, e.g., U.S. Pat. Nos. 3,780,425 and 3,781,176). Alternatively, if the device supplies current to the thermoelectric module 300, rather than receiving it, then it can produce heating or cooling of the first and second elements 304,302, depending upon the characteristics of the current flow. In this case the device 100 may produce heat, due to discharge of the battery in order to provide the thermal stimulation (i.e. cooling or heating of the brain). Energy reception plate 350d can be configured to transfer heat away from the device 100. Alternatively energy reception plate 350D can be configured to provide additional forms of wireless energy harvesting and can contain some or all of the necessary components to achieve this (although not shown, electrical conduits 306 C-E, and electrical contacts 354C-E can provide power and communication to be exchanged between energy receiver plate 350d and the device 100). Additionally, energy reception plate 350C can be configured to harness wireless energy and to supply energy to the thermal module in order to provide, for example, cooling of the brain.

FIG. 7 shows a rechargeable power supply 10 which is used for recharging a battery, for providing energy to a device 100, or for providing energy during thermal cooling of the brain which is disposed partially or fully in an extra-cranial location that is remote from an implanted device 100 which here is a neurostimulator. Energy harvesting and recharging as well as cooling-based neurostimulation therapy can produce heat as a by-product. Further, the discharge of a battery which is supplying power during thermal stimulation (i.e. neural-cooling) can result in heat generation within the battery. Deployment of the re-charging receiver plates 350c upon the patient's skull and otherwise removed somewhat from the device itself is advantageous since implanted devices often use the device "can" as a ground to which electrical sensors are referenced. Because charging operations may encounter relatively large fluctuations in power generation and storage, as well as thermal fluctuations, these should likely occur some distance from the device 100 itself.

FIG. 7 shows an embodiment of the invention in which a distally located wireless energy receiver module 350C, may be configured as an energy harvesting device 10 having modules such as 300, 330-336, and which contains a signal routing module 114b, for transmitting data and power through electrical conduits 306, and to device 100. When the energy harvesting device is a thermoelectric module 300, then energy can be created when the thermoelectric module experiences a temperature differential between its first element 304 which is on the ventral side and which obtains heat from intracranial sources, and a second element 302, which is disposed dorsally. Charge crossing the PN stack 305 causes current to flow through conductive conduits 306 an into the device 100 through electrical contacts housed under the electrical connection module 365. Electrical connection module also serves to connect a proximal side of neuron-stimulation leads 366 to the device 100, so that the distal side can be fed through burr hole 367 and into the brain of the patient. The device 100 may reside within a ferrule 352, which has been inserted in a prepared portion of the skull 351, and which is affixed to the skull with connection tabs 370. A first device cover 368 and a second device cover 369 can house the device components, and can also serve as energy harvesting antenna, or other components of the wireless energy harvesting modules. It is advantageous to have wireless energy harvesting devices (e.g. thermoelectric charging module) be remote from the neurostimulator since these may generate heat or conduct heat in a manner which makes the first and second surfaces similar in temperature.

It is one advantage of the current invention to provide an extra-cranially situated power harvester and/or rechargeable power supply which powers an intra-cranially situated, or skull mounted, device 100 which may be a neurostimulator. In a preferred embodiment, a portion of the recharging power related components are situated at least 0.5 inches away from the implanted device.

Wireless Energy Transmission and Reception Strategies.

Generally, the power received decreases with the amount of distance between the wireless transmitter and the receiver. While a skull mounted receiver plate 352 can assist in energy transfer with neurostimulation electrodes, when the implanted device is a cardiac-related device such preferential disposition of an wireless energy receiver such as an antenna will not help much. The transmission of energy, rather than energy reception, can have improved features which can assist in increasing wireless energy harvesting. A number of embodiments can serve to decrease the transmission distance and to increase patient compliance with respect to maintaining adequate charge levels.

In one embodiment the power transmitter can be implemented within modified versions of commonly used objects such as furniture. For example, a power transmitter can be located within:

a. a back of a chair and further with the transmitter situated approximately adjacent to the patient's upper torso;

b. a mattress or mattress cover and further with the transmitter situated approximately adjacent to the patient's upper torso;

c. a wearable vest, and further with the transmitter situated approximately adjacent to the patient's frontal and rear torso section;

d. an article of clothing such as a chest strap, brassier, wristband, armband, headband, or hat;

e. a blanket, blanket cover, or sheet, and further with the transmitter situated approximately adjacent to the patient's upper torso; and, f. a seat cushion configured to overlap or be attached to the back support portion of a chair and further with the transmitter situated approximately adjacent to the patient's upper torso.

Because it is wasteful to operate these types of power transmitters continuously, power transmission may be linked to a sensor which will automatically toggle the state of the power transmission. For example, a wireless power transmitter which is realized within a back of a chair may further comprise a motion sensor module, a temperature sensor module, a light sensor module, or a pressure sensor module, any of which may be used to determine if an individual (e.g., a patient with an implanted device) is sitting in the chair. The wireless power transmitter may also contain a sensor module which can receive an RF, sonic, or other signal from an implanted device that it is within the vicinity of the wireless power transmitter so that wireless power transmission may be initiated. The wireless power transmitter may also include a timer or real-time clock so that power transmission can occur for a selected amount of time, a selected amount of time after a patient activates a sensor module, during specific times of the day, and otherwise in manners that can be programmable and adjustable by the patient or a medical practitioner.

Although wireless power may be provided using far-field (e.g., RF) energy transmission, the above features can be implemented with transmission of other forms of wireless energy such as heat, light, induction, near and medium field transmission. In fact, induction type wireless charging is probably better suited for charging implanted devices if these are close enough to a body surface of the patient. Further, cooling devices may also be utilized in order to assist in thermoelectric power generation.

Wireless energy utilization can be realized by the implantable device using relatively new technologies for receiving the energy. Such technologies are related to inductive and far-field means of transmission and reception and include transmission by radiofrequency energy, thermal energy, sound energy, and other sources radiant energy. Schemes to achieve wireless energy transmission and harvesting is disclosed in US 2006/0281435 for 'power devices using RF energy harvesting', US20060270440 for a 'power transmission network' and a set of related disclosures filed by Shearer et al. and Greene et al, and which describe technology known as Powercast. The Powercast technology can be used for both transmission and reception (harvesting) of transmitted energy or of ambient energy such as radio-wave energy which is present in the devices environment. The Powercast technology can capture wireless energy using both near-field (e.g. inductive) and far-field transmitters. Alternative transmission-harvesting strategies have been described with sound or other energy types (e.g., U.S. Pat. No. 6,858,970 for a 'multi-frequency piezolelectric energy harvester', US 20050253152 for 'Non-contact pumping of light emitters via non-radiative energy transfer'), or resonant energy harvesters comprising resonant power antennas which tuned to the power transmitter's (beacon's) frequency in order to accomplish "nonradiative resonant energy transfer" (e.g. Soljacic et al. 2006, http://web.mit.edu/newsoffice/2006/wireless.html).

In order for implantable devices to effectively operate using wireless energy a number of considerations must be addressed. Firstly, the issue of energy reception should be addressed. When the energy harvesting module utilizes antennae larger volumes may be associated with improved energy capture. Further, although one energy harvester may be utilized, joint utilization of a plurality of harvesting modules can increase the amount and stability of the supplied power. Implanting the harvesting modules within the patient should be limited by issues related to implantation and explanation of the devices, patient comfort, and energy reception. Generally, the deeper implantation results in a corresponding decrease of energy reception for an equivalent amount of transmitted energy.

The human skull provides a unique location for implantation of energy harvesting components, including an antenna. In contrast to intracranial located positions, the surface of the skull provides a relatively large surface on which device components may reside. A skull mounted energy harvesting module has a number of benefits such as increased heat dissipation, increased energy transfer due to less intervening tissue, and increased capacity for retaining larger components. A preferred embodiment, skull mounted energy harvesting components may be configured according to the contours of a particular patient's skull, can be constructed in a flexible manner so that these may bend to the shape of the skull, or may be constructed in sections that are flexibly held together and which permit cooperation with the contour of the skull. The skull mounted energy harvesting device components can reside within a flexible and biocompatible material such as a silicone based sealant, or the like (Medtronic US20060184210 entitled 'explanation of implantable medical device'). In another embodiment, an implantable or intracranially residing neurostimulator is powered by an extracranially and approximately skull mounted harvesting device. In another embodiment, an implantable or intra-cranially residing neurostimulator is powered by a cranially residing skull mounted harvesting device, which may be affixed directly within the skull or indirectly via a ferrule device. Two or more energy harvesting devices, or related antennae, may be mounted bilaterally, over opposing hemispheres or split between frontal and posterior locations. The two or more antennae may be related to different uses such as wireless transmission/reception of data and power, respectively. Antennae may consist of various electroconductive harnessing substances such as metal, water, saline, saline laced with metallic flakes, or other suitable medium.

In one embodiment, recharging is halted or adjusted when non-charging operations such as sensing or stimulation operation are to occur. During sensing, this may be done in part to reduce any distortion of the sensed signals. For example, if the 'can' is serving as a ground for a mono-polar electrode, then if sensing occurs simultaneously with charging operations then the energy fluctuations associated with charging operations could distort, contaminate, or otherwise shift the recorded potentials.

For this reason, or due to other considerations, the implanted device could be triggered to send control commands to the wireless power harvester modules to turn energy harvesting 'on' or 'off'. Alternatively and additionally, the implanted device could send control commands to the wireless power transmitter to turn energy transmission 'on' or 'off', or can request that energy transmission be temporarily decreased or increased, or otherwise adjusted. Rather than simply shutting off, a temporarily increase or decrease can occur as a specified ramp-down or ramp-up function which may be related to charging operations or direct power supply to a in implanted device. Further, there can exist a "sleep" function which causes the power transmission to be stopped for a pre-defined amount of time before it is automatically restarted. In this manner, energy is not wasted by requiring the implanted device or the external patient programmer to send a 'restart' signal.

Rather than requiring the implanted device to send commands directly to a wireless power transmission device, the implanted device can control the wireless power transmitter indirectly through the external patient controller, which can be configured to communicate with the power transmitter as well as the implanted device. Additionally the external patient controller can be configured to send control signals to the wireless power transmitter in order to alter its activity, so that it may better perform its own operations. For example, the external patient controller can send control signals to the wireless power transmitter before it initiations communication with the implanted device or sends commands to the implanted device to initiate operations requiring stimulation or sensing. Rather than requiring wireless power companies to provide specialized transmitters that can receive commands from an external patient device, the wireless power transmitter can be power by a mains source which is fed to it by a programmable power supply created by a medical device manufacturer. Accordingly, a wireless power transmitter can be used, and a level of control can be obtained by controlling the power fed to the transmitter itself.

In one embodiment, the implanted device can provide alerts and status indications for level and power related characteristics such as the amount of power recently obtained, present power levels, or present strength of reception. Alternatively, or additionally the external patient programmer can also be configured with a wireless power harvester and/or 'power monitor' module adapted to measure the strength of transmitted energy that is being received, the amount of energy being harvested, or an energy profile which can contain an estimation of energy present at different wavelengths (e.g. a spectral profile of energy). Although the energy implanted wireless power components and external wireless power components may receive different amounts of energy, "Eint" and "Eext", respectively, these two amounts can be compared and a transfer function can be used to estimate the amount of energy actually received by the implanted harvester.

Additionally, the external patient controller can contain a "power profile" module which can adjust the amount of remaining "estimated power" for the implantable device by subtracting power which it estimates the internal device is consuming based upon the basal rate of energy usage of the device, notices it obtains from the implanted device that it has performed operations such as stimulating, and commands sent to the implanted device by the external device such as commands related to changing power state (e.g. going into a sleep state or commands to initiate stimulation or sensing operations).

Although the implanted wireless power harvester module may operate in a fixed manner, it may also adjust the characteristics of the harvester module in order to generate power from different frequencies of wireless energy which are present. The energy reception parameters can be adjusted to bias the reception of frequency specific energy so that reception of selected frequency ranges are facilitated or blocked. The energy harvester can utilize reception parameters which can be adjusted to match the frequencies of the energy which is received with the profile of energy being transmitted by a wireless power transmitter. This may occur because in different locations, different transmission profiles, reception profiles, or transmission-reception profiles will allow energy transmission, harvesting, or both to occur more efficiently or reliably or to provide different amount of energy as may be required by the implanted device. Further, when ambient levels of energy are relied upon, rather than wireless power transmitted energy, the spectral profile of the ambient energy may change over time and in different locations. Although the implanted device may automatically adjust the parameter of its harvesting module (which may occur with changes in the energy transmitting module) in order to adjust (i.e. improve) energy harvesting operations, this may require energy and could result temporary energy decreases (e.g. if an unsuccessful profile is selected). Accordingly the external patient programmer may perform these optimization/calibration processes and then use the results of these operations to adjust the characteristics of the implanted energy harvester.

Calibration test-signal procedures can be implemented when normal energy harvesting is not occurring. Additionally, in addition to using the external patient controller, an energy monitoring device (or only a sensor component) may be worn as a watch, or, in the case of a neurostimulator, can be incorporated into a person's hat or eyeglasses in order to sense energy fields which are similar to that which will be experienced by the implanted device.

Energy profile sensing can occur within the implanted or external energy monitoring devices in order to adjust parameters related to energy harvesting and increase or stabilize energy reception. While radiowaves may often be a main source of energy for the wireless power harvester device, if a patient is located in an area with larger sources of energy, then the wireless power harvester should be adjusted accordingly. For example, Extremely low frequency (ELF), voice frequency (VF), and very low frequency (VLF) may be ambient in an environment at higher levels than radiofrequency. Such an example occur in the case where a patient is situated in front of a television, so that 50 or 60 Hz line noise, and possibly the refresh rate of television screen, as well as the subharmonics and harmonics will be larger than radio-wave energy. At least one component of the energy harvester module should be configured to capture this type of energy and its harmonics. If the patient is outdoors in the country, then radiowaves may be larger than sources of 60 Hz, and the receiver should be tuned to optimize capture of this different energy profile. Additionally, the wireless power harvester module may contain two different harvesting circuits (e.g. including antennae and resonators) which are both active so that energy can be harvested at these very different locations of the electromagnetic spectrum.

The entire disclosure of all cited references including United States patents, applications, websites, and technical/scientific/engineering publications are hereby incorporated by reference into this specification as if fully recited herein. Using similar design features such as electrical or optical connections will be obvious to those skilled in the art, and it will also be obvious to those skilled in the art that the wireless power generation modules and process described herein may be scaled either up or down in size to suit power requirements of specific implantable devices. Any of the aforementioned changes may be made in the apparatus without departing from the scope of the invention as defined in the claims.

All section titles are provided for convenience and are merely descriptive and thereby are not intended to limit the scope of the invention.

What is claimed is:

1. A wirelessly powered medical system comprising:
   a wireless power transmitter; and
   an implantable medical device comprising:
   a wireless energy harvesting module configured for harvesting at least one type of wireless power;
   a power management module configured for managing, monitoring, and storing harvested power harvested by the energy harvesting module;
   a control module configured for controlling the power management module and for creating and storing in a memory module a historical power record, said record comprising at least one of amount of harvested wireless power and amount of power consumed as a function of time; and
   a communication module configured for providing communication between the implantable medical device and at least one external device.

2. The system of claim 1, wherein the external device is an external patient controller that is configured to provide communication between the implantable medical device and the wireless power transmitter.

3. The system of claim 1, wherein the external device is an external patient controller that is configured to display at least one historical value, the value being related to at least one of power harvesting and power consumption, said value based upon data from the historical power record that is communicated to the external patient controller from the implanted device.

4. The system of claim 3, wherein the at least one historical value is a historical record of the amount of energy that was harvested by the device as a function of time.

5. The system of claim 3, wherein the at least one historical value is a historical record of the amount of energy that was consumed by the device as a function of time.

6. The system of claim 3, wherein the at least one historical value is a historical record of wireless power harvesting calculated for at least one prior period that is selected to be at least one of a prior day, week, and month.

7. The system of claim 3, wherein the at least one historical value is a historical record that includes usage patterns calculated for prior periods including at least one of the prior day, week, and month.

8. The system of claim 1, wherein the external device is an external patient controller that is configured to display at least one historical value reflecting harvested energy as well as an indicator of a target amount of energy which should have been harvested.

9. The system of claim 8, wherein the target amount of energy which should have been harvested is defined as a function of time.

10. The system of claim 8, wherein the target amount of energy to be harvested is a value that is programmably defined and adjustable.

11. The system of claim 8, wherein the target amount of energy to be harvested is a value that is calculated upon data sensed by a sensor located in the external device.

12. The system of claim 8, wherein the target amount of energy to be harvested is a value that is calculated upon data sensed by a sensor located in the external device using a transfer function to estimate the amount of energy that should have actually been received by the harvesting module of the implanted device.

13. The system of claim 1, wherein the control module is further configured to control an alert module to provide an alert if energy harvesting increases above a specified level.

14. The system of claim 1, wherein the control module is further configured to control an alert module to provide an alert if energy harvesting decreases below a specified level.

15. The system of claim 1, wherein the control module is further configured to control an alert module to provide an alert if energy harvesting decreases below a specified level for at least a selected duration.

16. The system of claim 1, wherein the control module is further configured to control an alert module to provide an alert if energy harvesting fails to meet at least one energy generation criterion.

17. The system of claim 1, wherein the control module is further configured to adjust operation of the implanted device, when the power falls to a selected critical level.

18. The system of claim 1, wherein the control module is further configured to shut down to a low power state, when the power falls to a selected critical level.

19. The system of claim 18, wherein the control module is further configured for storing power 'shut-downs' and 'restarts' in a memory module, whereby a record of insufficient energy harvesting is created.

20. The system of claim 1, wherein the transmitter is configured for resonant energy transfer.

21. The system of claim 1, wherein the energy harvesting module is configured for resonant energy harvesting.

22. The system of claim 1, wherein the energy harvesting module is configured for RF energy harvesting.

23. The system of claim 1, wherein the external device is configured to provide communication between the implantable medical device and the wireless power transmitter.

* * * * *